United States Patent
Garcia Molina et al.

(10) Patent No.: US 12,016,698 B2
(45) Date of Patent: Jun. 25, 2024

(54) SYSTEM AND METHOD FOR FACILITATING SLEEP IMPROVEMENT FOR A USER

(71) Applicant: KONINKLIJKE PHILIPS N.V., Eindhoven (NL)

(72) Inventors: Gary Nelson Garcia Molina, Madison, WI (US); Edouard Robert Marcus Gebski, Pittsburgh, PA (US); Mark Choi, Monroeville, PA (US); Annette Kapitan, Monroeville, PA (US); Stefan Pfundtner, Eindhoven (NL); Tsvetomira Kirova Tsoneva, Eindhoven (NL); Anandi Mahadevan, Murrysville, PA (US); Megan King, Pittsburgh, PA (US); Diane Kosobud, Montgomery, OH (US); Jessica Weeden, Monroeville, PA (US); Guy Anthony Brown, Haarlem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 148 days.

(21) Appl. No.: 16/008,102

(22) Filed: Jun. 14, 2018

(65) Prior Publication Data
US 2019/0083028 A1   Mar. 21, 2019

Related U.S. Application Data

(60) Provisional application No. 62/520,063, filed on Jun. 15, 2017.

(51) Int. Cl.
*A61B 5/00* (2006.01)
*A61M 21/02* (2006.01)
(Continued)

(52) U.S. Cl.
CPC .......... *A61B 5/4815* (2013.01); *A61B 5/4806* (2013.01); *A61M 21/02* (2013.01);
(Continued)

(58) Field of Classification Search
CPC ....... G16H 50/30; A61B 5/4806–4815; A61M 21/00–02; A61M 2021/0005–0088
See application file for complete search history.

(56) References Cited

U.S. PATENT DOCUMENTS 6,120,441 A * 9/2000 Griebel .................. A61B 5/113
600/300
6,878,121 B2 * 4/2005 Krausman ............. A61B 5/1118
600/587

(Continued)

FOREIGN PATENT DOCUMENTS

| CN | 105231997 A | 1/2016 |
| CN | 105796061 A | 7/2016 |

OTHER PUBLICATIONS

Harvard Health Publishing. "Restructure your day to get a better night's sleep", Aug. 1, 2015. Accessed Jan. 25, 2023 from https://www.health.harvard.edu/sleep/restructure-your-day-to-get-a-better-nights-sleep#:~:text=Keep%20a%20regular%20schedule%20for, Dorsey. (Year: 2015).*

(Continued)

*Primary Examiner* — Christine H Matthews

(57) ABSTRACT

The present disclosure pertains to facilitating sleep improvement for a user. In a non-limiting embodiment, user data associated with a sleep session of a user is received from one or more sensors. Based on the user data, one or more sleep metrics associated with the sleep session are generated. One or more reference sleep metrics are determined based on prior user data obtained from one or more prior sleep sessions. One or more immediate values related to the sleep session is/are determined based on a comparison of the sleep (Continued)

metrics with the reference sleep metrics. A sleep session score value is generated based on the immediate values, and the sleep session score value and the sleep metrics are caused to be presented on via an output device.

34 Claims, 12 Drawing Sheets

(51) Int. Cl.
*G16H 20/70* (2018.01)
*G16H 50/20* (2018.01)
*G16H 50/30* (2018.01)
*A61M 21/00* (2006.01)

(52) U.S. Cl.
CPC ............ *G16H 20/70* (2018.01); *G16H 50/20* (2018.01); *G16H 50/30* (2018.01); *A61B 5/4812* (2013.01); *A61M 2021/0022* (2013.01); *A61M 2021/0027* (2013.01); *A61M 2021/0044* (2013.01); *A61M 2021/0055* (2013.01); *A61M 2021/0066* (2013.01); *A61M 2021/0083* (2013.01); *A61M 2205/332* (2013.01); *A61M 2205/3375* (2013.01); *A61M 2205/3553* (2013.01); *A61M 2205/3584* (2013.01); *A61M 2205/505* (2013.01); *A61M 2230/06* (2013.01); *A61M 2230/10* (2013.01); *A61M 2230/18* (2013.01); *A61M 2230/42* (2013.01); *A61M 2230/63* (2013.01)

(56) References Cited

U.S. PATENT DOCUMENTS

| | | | | |
|---|---|---|---|---|
| 2005/0143617 | A1* | 6/2005 | Auphan | A61B 5/08 600/26 |
| 2005/0267362 | A1* | 12/2005 | Mietus | A61B 5/087 600/429 |
| 2010/0049008 | A1* | 2/2010 | Doherty | A61M 16/024 600/301 |
| 2010/0197996 | A1 | 8/2010 | Cornel | |
| 2011/0010014 | A1* | 1/2011 | Oexman | F24F 11/0001 700/276 |
| 2017/0189641 | A1 | 7/2017 | Moturu et al. | |

OTHER PUBLICATIONS

P. R. T. Ko, J. A. Kientz, E. K. Choe, M. Kay, C. A. Landis, and N. F. Watson, "Consumer sleep technologies: A review of the landscape," J. Clin. Sleep Med., vol. 11, No. 12, pp. 1455-1461, 2015.
W. Liu, B. Ploderer, and T. Hoang, "In Bed with Technology: Challenges and Opportunities for Sleep Tracking," in Proceedings of the Annual Meeting of the Australian Special Interest Group for Computer Human Interaction on—OzCHI '15, 2015, pp. 142-151.

* cited by examiner

SYSTEM AND METHOD FOR FACILITATING SLEEP IMPROVEMENT FOR A USER

CROSS-REFERENCE TO PRIOR APPLICATIONS

This application is the U.S. National Phase application which claims the benefit of U.S. Provisional Patent Application No. 62/520,063, filed 15 Jun. 2017 and European Patent Application No. 17191471.6, filed on 15 Sep. 2017. These applications are hereby incorporated by reference herein.

BACKGROUND

1. Field

The present disclosure pertains to a system and method for facilitating sleep improvement for a user.

2. Description of the Related Art

Systems for monitoring sleep are known. Many sleep monitoring systems lack the ability to provide a meaningful and quantifiable metric for an individual to understand a quality of his/her sleep. Furthermore, many sleep monitoring systems lack the ability to provide mechanisms for encouraging healthy sleep habits. The present disclosure overcomes deficiencies in such systems.

SUMMARY

Accordingly, one or more aspects of the present disclosure relate to a method for facilitating sleep improvements for a user. The method includes receiving, from one or more sensors, first user data associated with a first sleep session of a user. Based on the first user data, one or more first sleep metrics associated with the sleep session are determined. The method includes determining one or more reference sleep metrics, the one or more reference sleep metrics being based on prior user data obtained from one or more prior sleep sessions. One or more first immediate values related to the first sleep session is determined, the determination of the one or more first immediate values being based on a comparison of the one or more first sleep metrics with the one or more reference sleep metrics. A first sleep session score value is generated based on the one or more immediate values related to the first sleep session, and the first sleep session score value and the one or more first sleep metrics are caused to be presented via an output device.

Another aspect of the present disclosure relates to a sleep score assessment system for facilitating sleep improvement of a user. The system includes memory, communications circuitry, and one or more processors configured by machine-readable instructions stored by the memory to receive, from one or more sensors, first user data associated with a first sleep session of a user. Based on the first user data, one or more first sleep metrics associated with the sleep session are determined. The one or more processors are configured by the machine-readable instructions to determine one or more reference sleep metrics, the one or more reference sleep metrics being based on prior user data obtained from one or more prior sleep sessions, and determine one or more first immediate values related to the first sleep session, the determination of the one or more first immediate values being based on a comparison of the one or more first sleep metrics with the one or more reference sleep metrics. The one or more processors are configured by the machine-readable instructions to generate a first sleep session score value based on the one or more immediate values related to the first sleep session, and cause the first sleep session score value and the one or more first sleep metrics are caused to be presented via an output device.

Yet another aspect of the present disclosure relates to a sleep score assessment system configured to facilitate sleep improvement for a user. The sleep score assessment system includes means for receiving, from one or more sensors, first user data associated with a first sleep session of a user, means for determining, based on the first user data, one or more first sleep metrics associated with the first sleep session, means for determining one or more reference sleep metrics, the one or more reference sleep metrics being based on prior user data obtained from one or more prior sleep sessions, means for determining one or more first immediate values related to the first sleep session, the determination of the one or more first immediate values being based on a comparison of the one or more first sleep metrics with the one or more reference sleep metrics, means for generating a first sleep session score value based on the one or more first immediate values related to the first sleep session, and means for causing the first sleep session score value and the one or more first sleep metrics to be presented via an output device.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
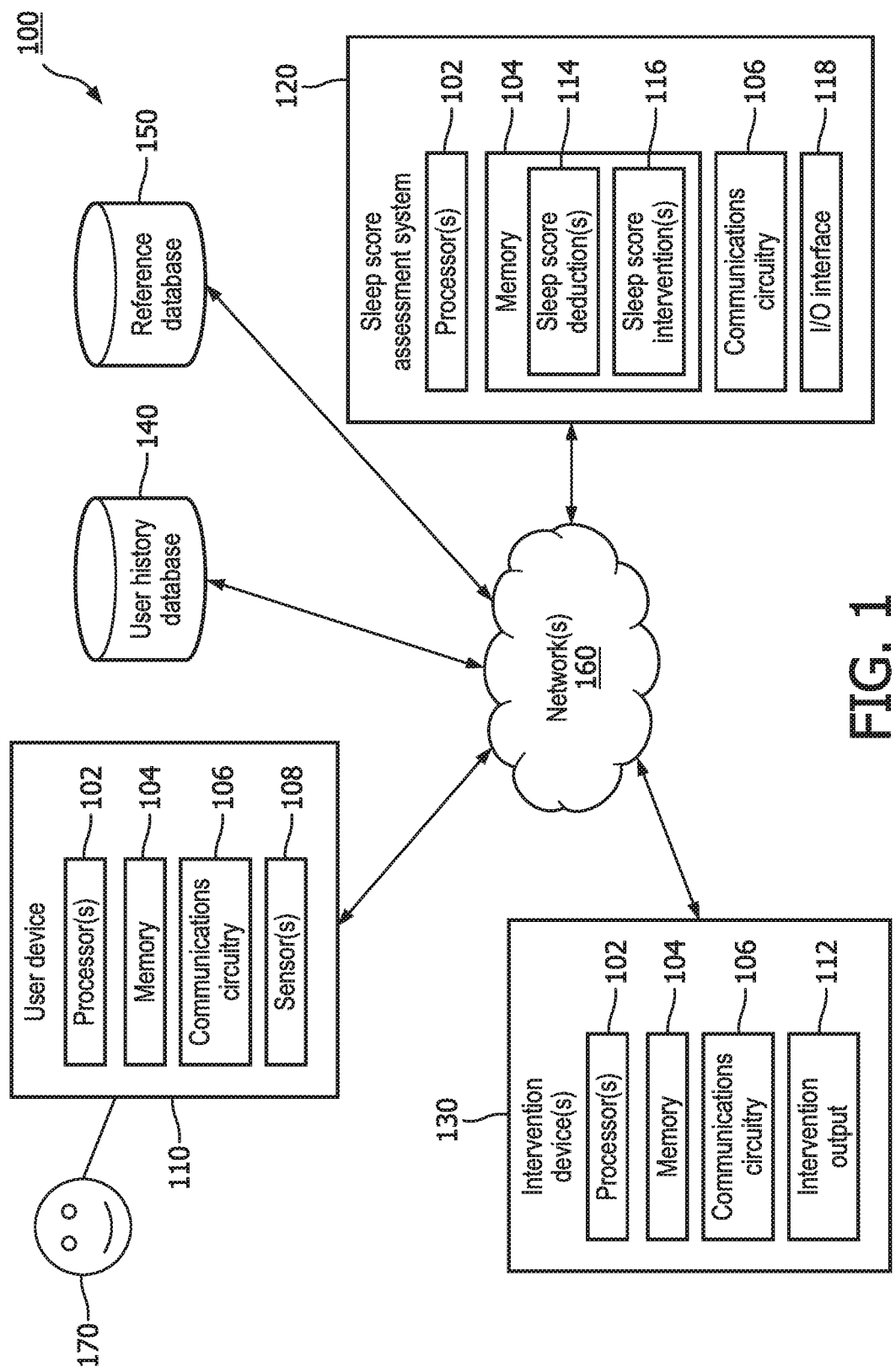
FIG. 1 is a schematic illustration of an exemplary system configured to facilitate sleep improvement for an individual, in accordance with various embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of an exemplary system 100 configured to facilitate sleep improvement for an individual, in accordance with various embodiments. System 100, in a non-limiting embodiment, includes a user device 110, a sleep score assessment system 120, and one or more intervention devices 130. Each of user device 110, sleep score assessment system 120, and intervention device(s) 130 are capable of communicating with one another via one or more network(s) 160. For example, user device 110 and sleep score assessment system 120 may communicate over an intranet and/or the Internet. Furthermore, in one embodiment, system 100 includes a user history database 140 and a reference database 150.

In the illustrative embodiment, user device 110 is configured to monitor activity of a user 170 and store inputs detected by one or more sensors 108. Sensor(s) 108 correspond to any suitable sensor capable of measuring one or more parameters of user 170. For example, sensor(s) 108 may correspond to one or more accelerometers, one or more gyroscopes, one or more pulse rate monitors, one or more breath monitoring devices, and/or one or more electroencephalography ("EEG") devices. However, persons of ordinary skill in the art will recognize that user device 110 may include any additional type of sensor, or any combination thereof. In one embodiment, sensor(s) 108 are configured to take measurements at predefined temporal intervals. For instance, sensor(s) 108 may be configured (e.g., by processor(s) 102 using instructions stored by memory 104) to take a "sample" measurement every second. A sampling rate—how often sensor(s) 108 take a measurement—is configurable by user device 110 and can depend on a type of sensor that sensor(s) 108 correspond to, as well as a type of measurement that sensor(s) 108 is attempting to obtain. Furthermore, sensor(s) 108 are capable of being configured by user 170 and/or by one or more other devices of system 100 (e.g., sleep score assessment system 120) to modify a sample rate for sensor(s) 108 depending on a particular functionality desired.

User device 110, in one embodiment, corresponds to any suitable type of electronic device including, but are not limited to, desktop computers, mobile computers (e.g., laptops, ultrabooks, etc.), mobile phones, smart phones, tablets, personal digital assistants ("PDAs"), and/or wearable devices (e.g., watches, pins/broaches, headphones, etc.). Furthermore, in the illustrative embodiment, user device 110 includes one or more processors 102, memory 104, and communications circuitry 106.

Processor(s) 102 include any suitable processing circuitry capable of controlling operations and functionality of user device 110, as well as facilitating communications between various components within user device 10. In one embodiment, processor(s) 102 may include a central processing unit ("CPU"), a graphic processing unit ("GPU"), one or more microprocessors, a digital signal processor, or any other type of processor, or any combination thereof. In another embodiment, the functionality of processor(s) 102 is performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 102 is capable of including its own local memory, which may store program systems, program data, and/or one or more operating systems. However, processor(s) 102 are capable of running an operating system ("OS") for user device 110, and/or one or more firmware applications, media applications, and/or applications resident thereon. In one example embodiment, processor(s) 102 runs a local client script for reading and rendering content received from one or more websites. For example, processor(s) 102 may run a local JavaScript client for rendering HTML or XHTML content.

Memory 104, in one embodiment, includes one or more types of storage mediums such as any volatile or non-volatile memory, or any removable or non-removable memory implemented in any suitable manner to store data for user device 110. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 104 may be implemented as computer-readable storage media ("CRSM"), which may be any available physical media accessible by processor(s) 102 to execute one or more instructions stored within memory 104. In an example embodiment, one or more applications (e.g., gaming, music, video, calendars, lists, etc.) are run by processor(s) 102, and may be stored in memory 104.

Communications circuitry 106, in one embodiment, corresponds to any circuitry allowing or enabling one or more components of user device 110 to communicate with one another, and/or with one or more additional devices, servers, and/or systems (e.g., sleep score assessment system 120 and/or intervention device(s) 130). As an illustrative example, user data corresponding to readings obtained by sensor(s) 108 may be transmitted over a network 160, such as the Internet, to sleep score assessment system 120 using any number of communications protocols. For example, network(s) 160 are capable of being accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between user device 110, sleep score assessment system 120, and/or intervention device(s) 130. In one embodiment, user device 110, sleep score assessment system 130, and/or intervention device(s) 130 communicate with one another via a web browser using HTTP. Various additional communication protocols used to facilitate communications between one or more devices of system 100 include, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP. Communications circuitry 106 is capable of using communications protocol, such as any of the previously mentioned exemplary communications protocols. In one embodiment, user device 110 includes one or more antennas to facilitate wireless communications with a network using various wireless technologies (e.g., Wi-Fi, Bluetooth, radiofrequency, etc.). In yet another embodiment, user device 110 includes one or more universal serial bus ("USB") ports, one or more Ethernet or broadband ports, and/or any other type of hardwire access port so that communications circuitry 106 allows user device 110 to communicate with one or more communications networks (e.g., network(s) 160).

As illustrated by FIG. 1, as user 170 sleeps, user device 110—and in particular sensor(s) 108—monitor sleep activity. In one embodiment, user device 110 is configured to send user data associated with a first sleep session of user 170 to sleep score assessment system 120. For example, user data indicating an activity of user 170 during a first sleep session may be sent to sleep score assessment system 170 via network(s) 160. In one embodiment, the user data is provided to sleep score assessment system 120 at an end of the sleep session, however this is merely exemplary as the user data is capable of being provided to sleep score assessment system 120 periodically (e.g., every 5-10 minutes), and persons of ordinary skill in the art will recognize that the aforementioned is merely exemplary.

Sleep score assessment system 120, in the non-limiting embodiment, includes processor(s) 102, memory 104, communications circuitry 106, and an I/O (input/output) interface 118. Processor(s) 102, memory 104, and communications circuitry 106 of sleep score assessment system 120 are, in one embodiment, substantially similar to processor(s) 102, memory 104, and communications circuitry 106 of user device 110, and the previous description may apply.

I/O interface 118 is capable of corresponding to any suitable input and/or output component such as, and without limitation, one or more microphones or other audio input devices, one or more speakers or other audio output devices, one or more input mechanisms (e.g., buttons, knobs, switches, etc.), one or more cameras or other image capture devices, and/or one or more display screens. For example, sleep score assessment system 120 may include a display screen of any suitable size and/or shape. Various types of displays include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. I/O interface 108 further is capable of including a touch screen, such as a touch screen including capacitive sensing panels capable of recognizing touch inputs thereon. For instance, a touch screen may correspond to a projected capacitive touch ("PCT"), screen include one or more row traces and/or driving line traces, as well as one or more column traces and/or sensing lines.

In the non-limiting embodiment, memory 104 includes instructions for determining a sleep score of user 170 for a particular sleep session. The sleep score is capable of being determined based on one or more sets of instructions or rules stored within memory 104 such as rules/instructions associated with one or more sleep score deductions 114 and/or rules/instructions associated with one or more sleep score interventions. Sleep score assessment system 120 is configured to receive the user data associated with a sleep session and determine one or more sleep metrics associated with the first sleep session. For example, sleep architecture, sleep continuity, a sleep onset, and/or a sleep wakeup time are all exemplary types of metrics capable of being determined for a particular sleep session. The sleep architecture, for instance, includes duration of each sleep stage (e.g., N3, N2, N1, REM), a latency of each sleep stage, and/or a survival curve of each sleep stage.

As described in greater detail below, sleep score assessment system 120 is configured, in one embodiment, to determine a type and amount of sleep score deductions user the rules/instructions associated with sleep score deductions 114. To determine the sleep score deductions, one or more reference sleep metrics are employed and compared with the sleep metrics determined using the user data. In one embodiment, the reference sleep metrics are obtained from user history database 140 and/or reference database 150.

User history database 140 stores information associated with a user's sleep history. For example, user history database 140 may store information indicating a time or times of sleep onset for a particular user, a time or times of sleep wakeup, and the like. In a non-limiting embodiment, historical sleep information for a particular user is stored by user history database 140, and is accessible by sleep score assessment system 120 via network 160.

Reference database 150 stores information associated with referential data pertaining to user 170. For example, reference database 150 may store sleep information associated with an age of user 170, a gender of user 170, a chronotype of user 170, and the like. In a non-limiting embodiment, reference sleep information associated with user 170 is stored by reference database 150, and is accessible by sleep score assessment system 120 via network 160.

In the non-limiting example embodiment, sleep score assessment system 120 is configured to determine a number of deductions associated with a particular sleep session, and an amount (e.g., a severity/magnitude) of each deduction. To do this, as described in greater detail below, a comparison between the sleep metrics associated with a particular sleep session and the reference sleep metrics (e.g., user history sleep information, reference sleep information) that have previously been obtained may be performed. Sleep score assessment system 120 is configured to use these comparisons to determine one or more immediate values related to the first sleep session. For example, the immediate values may correspond to one or more deductions to be applied to a sleep score.

In a non-limiting example embodiment, five different types of sleep deductions are capable of being implemented by rules/instructions associated with sleep score deductions 114. In this embodiment, the deductions correspond to one or more of a total sleep time, a total time spent away between a sleep onset time and a sleep offset time (e.g., a wake after sleep onset ("WASO"), a number of sleep disruptions that occurred during a sleep session (e.g., a period of wakefulness exceeding a threshold amount of time between sleep onset and sleep offset), a sleep routine that depends on a regularity of sleep onset and wakeup times, a sleep onset latency (e.g., a duration of time to sleep onset), and a deduction based on N3, also referred to as deep sleep. Persons of ordinary skill in the art will recognize that the aforementioned list of sleep deduction types is merely exemplary, and more or fewer sleep deductions types may be employed.

In an exemplary embodiment, sleep score assessment system 120 starts with an initial sleep session score value. For each deduction identified within a particular sleep session, the deduction is added to the initial sleep session score value. In one embodiment, the deductions are negative in value (e.g., <0), however persons of ordinary skill in the art will recognize that this is merely exemplary. For example, each deduction may, alternatively, be subtracted from the initial sleep session score value. In this particular scenario, the deductions are positive in value (e.g., >0). After applying (e.g., adding/subtracting) each deduction to the initial sleep session score value, a new sleep session score value is obtained. In one embodiment, the new sleep session score value is capable of being provided to user 170 via I/O interface 118. For example, if I/O component 118 includes a display device, sleep score assessment system 120 is capable of causing the new sleep session score value to be presented on a graphical user interface via the display device. In one embodiment, in addition to the new sleep session score value, the sleep metrics associated with the sleep session are also presented such that user 170 is capable of viewing what factors caused his/her sleep session score to be a particular value. For example, user 170 may view a number of times that he/she was awake, which may have caused the sleep session score value to be the determined value. Persons of ordinary skill in the art will recognize that although the aforementioned describes that the new sleep session score value is presented via I/O interface 118 of sleep score system 120, this is merely exemplary as the sleep session score value may alternatively be provided to user device 110, or any other device, for consumption by user 170.

In the illustrative embodiment, system 100 further includes one or more intervention devices 130. Each of intervention devices 130 includes processor(s) 102, memory 104, and communications circuitry 106, which are substantially similar to processors 102, memory 104, and communications circuitry 106 of user device 110, and the previous descriptions apply. Furthermore, each intervention device 130 includes one or more intervention output components 112. Intervention output component(s) 112, in one embodiment, correspond to any suitable sleep intervention component including, but not limited to, one or more auditory stimulation devices, one or more visual stimulation devices, one or more haptic stimulation devices, one or more closed-loop sleep induction devices, one or more smart wakeup devices, and the like. In one example embodiment, intervention output component 112 corresponds to a thermal connection component capable of adjusting a temperature of a local environment with which user 170 is located. For example, intervention output component 112 is capable of adjusting a thermostat in a user's household. Persons of ordinary skill in the art will also recognize that some intervention devices 130 are configured to include two or more intervention output components 112 and although only a single intervention device 130 is displayed within system 110, two or more intervention devices may be included. Further still, intervention device(s) 130 are capable of communicating with one or more of user device 110 and/or sleep score assessment system 120 via network 160.

In a non-limiting embodiment, one or more sleep interventions that occurred via intervention device(s) 130 during a sleep session are determined based on the user data that has been obtained. For instance, and as described in greater detail below, if one or more sleep interventions have occurred during the first sleep session, then the user data obtained by sensor(s) 108 may indicate this and therefore sleep score assessment system 120 may identify the intervention(s) within the user data. In one embodiment, intervention device(s) 130 are also capable of communicating the particular intervention that was performed to sleep score assessment system 120 via network(s) 160. The various types of interventions that may be performed include, but are not limited to, one or more audible tones provided during the sleep session, one or more visual signals provided during the sleep session, one or more haptic signals provided during the sleep session, and/or one or more environmental interventions. For example, the audible tones may be output by an auditory stimulation device (e.g., an audible alarm clock, music player, etc.), the visual signals may be output by a visual stimulation device (e.g., white light-emitting devices, warm/calm light-emitting devices, etc.), the haptic signals may be output by a haptic stimulation device (e.g., vibration plate, a wearable tactile stimulator, etc.), and the environmental interventions may be provided by an environmental control device.

Upon identifying the intervention that occurred, sleep score assessment system 120 may be configured to use the rules/instructions associated with sleep score interventions 116 to determine a number of sleep interventions and a magnitude/amount of those sleep interventions. The interventions, in one embodiment, are applied to improve an aspect, or aspects, of sleep. For example, an auditory stimulation may enhance deep sleep, and a sleep induction intervention shortens sleep onset latency. Each of the sleep interventions may be applied to the initial sleep session score value (or the sleep session score value including the deductions, as described above), to generate a new sleep session score value. For example, the sleep interventions may be represented as a bonus applied to an initial sleep score to increase the sleep session score value in a manner akin to the sleep deductions being applied to the initial sleep score to decrease the sleep session score value. In one embodiment, each intervention may be added to the sleep session score to obtain the new sleep session score value. In one embodiment, a value associated with each sleep intervention is positive, such that the interventions contribute positively to the sleep session score value. However, persons of ordinary skill in the art will recognize that, similar to the sleep deductions, sleep interventions may contribute positively or negatively to the sleep session score, and the aforementioned is merely exemplary. As seen from Equation 1, the sleep session score value is capable of being determined where:

Sleep_Session_Score_Value=Initial_Sleep_Score+ Sleep_Deductions+ΣSleep_Interventions    Equation 1.

In Equation 1, Initial_Sleep_Score corresponds to an exemplary initial sleep session score value, such as the number 100, Σ Sleep_Deductions corresponds to a sum of all of the sleep deduction values (e.g., where each deduction is negative in value), and Σ Sleep_Interventions corresponds to a sum of all of the sleep intervention values (e.g., where each intervention is positive in value).

Persons of ordinary skill in the art will recognize that although system 100 of FIG. 1 is illustrated such that each of user device 110, sleep score assessment system 120, intervention device(s) 130, user history database 140, and reference database 150 are separate, some or all of the aforementioned may be located in a single device, or spread about multiple devices. For example, sleep score assessment system 120 may, in one embodiment, include one or more of sensor(s) 118 and/or intervention output(s) 112. As another example, user history database 140 and/or reference database 150 may be stored locally within memory 104 of sleep score assessment system 120.

Figure 2:
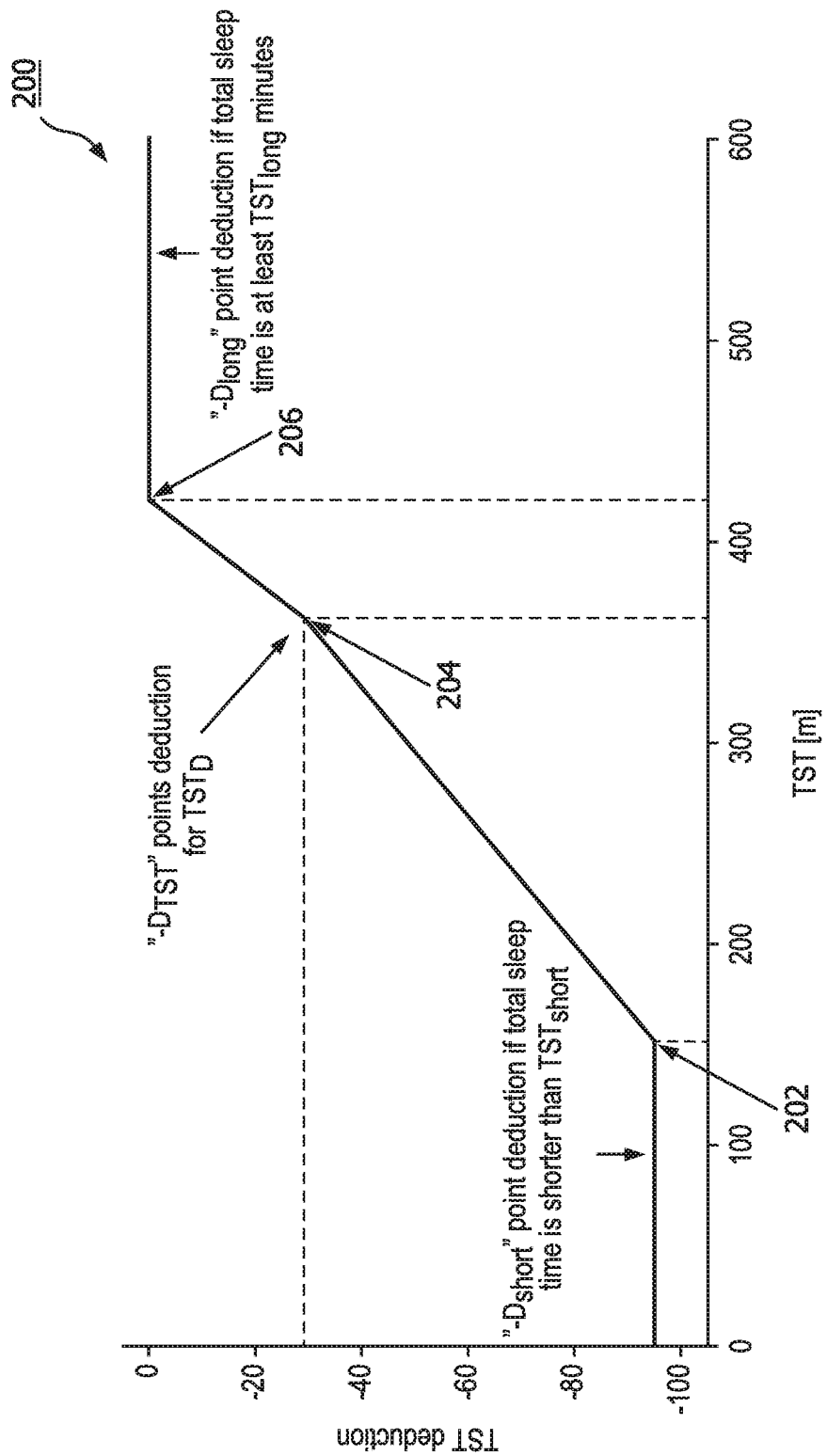
FIG. 2 is an illustrative graph of a technique for determining a total sleep time deduction, in accordance with various embodiments.

FIG. 2 is an illustrative graph 200 of a technique for determining a total sleep time deduction, in accordance with various embodiments. In one embodiment, a total sleep time ("TST") corresponds to an amount of time that user activity, detected by sensor(s) 108, is determined to be sleep. If the TST is greater than (or equal to) a predefined threshold value for TST, then sleep score assessment system 120 is configured to apply a deduction equal to zero. For example, if a TST for a sleep session is determined to be greater than 8 hours in duration, then an amount of deductions for TST may be zero. This parameter may be configurable by user 170 and/or system 120. However, if the TST is less than the predefined threshold value for TST, then sleep score assessment system 120 is configured to apply a particular deduction. This deduction, for instance, is associated with a total duration of the TST and thus is configured such that, depending on the total duration of the TST, the deduction differs.

As seen in graph 200, for TST durations that are less than or equal to a first threshold 202 (e.g., $TST_{short}$), a first deduction $D_{short}$ is to be applied by sleep score assessment system 120. For example, if the amount of time of sleep is less than 150 minutes, rules/instructions associated with sleep deductions 114 may indicate that a deduction of −95 is to be applied, where $D_{short}=95$. If a TST duration is greater than or equal to first threshold 202 but less than a second threshold 204 (e.g., $TST_D$), then a second deduction is to be applied. The second deduction, in one embodiment, is linearly related to the TST duration, as described in greater detail below with reference to Equation 2. If a TST duration is greater than or equal to second threshold 204 but less than a third threshold 206 (e.g., $TST_{long}$), then a third deduction is to be applied. The third deduction, similarly to the second deduction, is linearly related to the TST duration, as described in greater detail with reference to Equation 2. Finally, if a TST duration is greater than third threshold 206, a fourth deduction $D_{long}$ is to be applied. Persons of ordinary skill in the art will recognize that each of threshold 202, 204, and 206 may be configurable depending on the particular user, and furthermore may be updated overtime based on a user history, and the aforementioned and below are merely illustrative example.

$$TST \text{ deduction} = \begin{cases} -D_{short} & TST < TST_{short} \\ \text{round}\left(-D_{short} + \frac{(-D_{TST} + D_{short}) \times (TST - TST_{short})}{TST_D - TST_{short}}\right) & TST_{short} \leq TST < TST_D \\ \text{round}\left(-D_{TST} + \frac{(-D_{long} + D_{TST}) \times (TST - TST_D)}{TST_{long} - TST_D}\right) & TST_D \leq TST < TST_{long} \\ -D_{long} & TST_{long} \leq TST \end{cases} \quad \text{Equation 3}$$

Table 1 is a table illustrating exemplary values for $TST_{short}$, $TST_D$, $TST_{long}$, $D_{short}$, $D_{TST}$, and $D_{long}$, in accordance with various embodiments. Persons of ordinary skill in the art will recognize that these values are merely illustrative, and may be configured by user 170 and/or system 120.

TABLE 1

| Parameter | Default value |
|---|---|
| $TST_{short}$ | 150 minutes |
| $TST_D$ | 360 minutes |
| $TST_{long}$ | 420 minutes |
| $D_{short}$ | 95 |
| $D_{TST}$ | 30 |
| $D_{long}$ | 0 |

Figure 3:
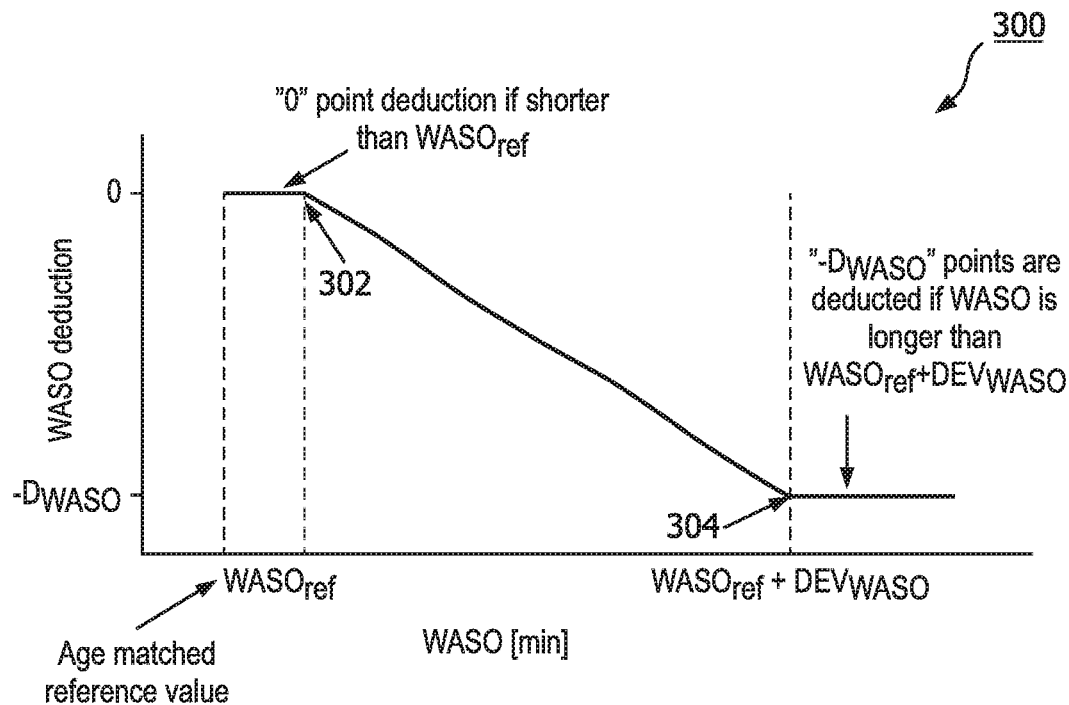
FIG. 3 is an illustrative graph of a technique for determining a deduction associated with a total time spent awake, in accordance with various embodiments.

FIG. 3 is an illustrative graph 300 of a technique for determining a total time spent awake deduction, in accordance with various embodiments. A total amount of time that an individual is awake after sleep onset ("WASO") is, in one embodiment, another measure with which deductions are capable of being applied to a sleep session score. WASO includes not only time awake, but also micro-arousals, and more generally any amount of time that a user spends awake (e.g., user activity detected by sensor(s) 108 exceeding a threshold value) after sleep onset is identified.

In one embodiment, a deduction based on WASO depends on an age of user 170, as seen below with reference to Table 2. The age of user 170 indicates a reference value, $WASO_{ref}$, which corresponds to a maximum WASO duration before deductions are to be applied. The deduction is maximal a detected WASO exceeds $WASO_{ref}$ by a threshold amount $DEV_{WASO}$. In the exemplary embodiment, WASO and $DEV_{WASO}$ are defined in minutes, however persons of ordinary skill in the art will recognize that this is merely exemplary.

TABLE 2

| Age Range | $WASO_{ref}$ [minutes] |
|---|---|
| >30 | 20 |
| [30 to 40[ | 20 |
| [40 to 60[ | 40 |
| ≥60 | 70 |

In the illustrative embodiment, a deduction of zero is applied if the WASO amount of time is less than a first threshold 302, indicated by $WASO_{Ref}$. If, the WASO amount of time is greater than a second threshold 304, then a largest deduction $-D_{WASO}$ is applied. In one embodiment, if the WASO amount of time is less than second threshold 304 but greater than threshold 302, then Equation 3 is applied to determine a deduction value to be used.

$$WASO\ deduction = \text{round}\left(\max\left\{-D_{WASO}, \min\left\{0, -\frac{D_{WASO} \times (WASO - WASO_{ref})}{DEV_{WASO}}\right\}\right\}\right).$$ Equation 3

Figure 4:
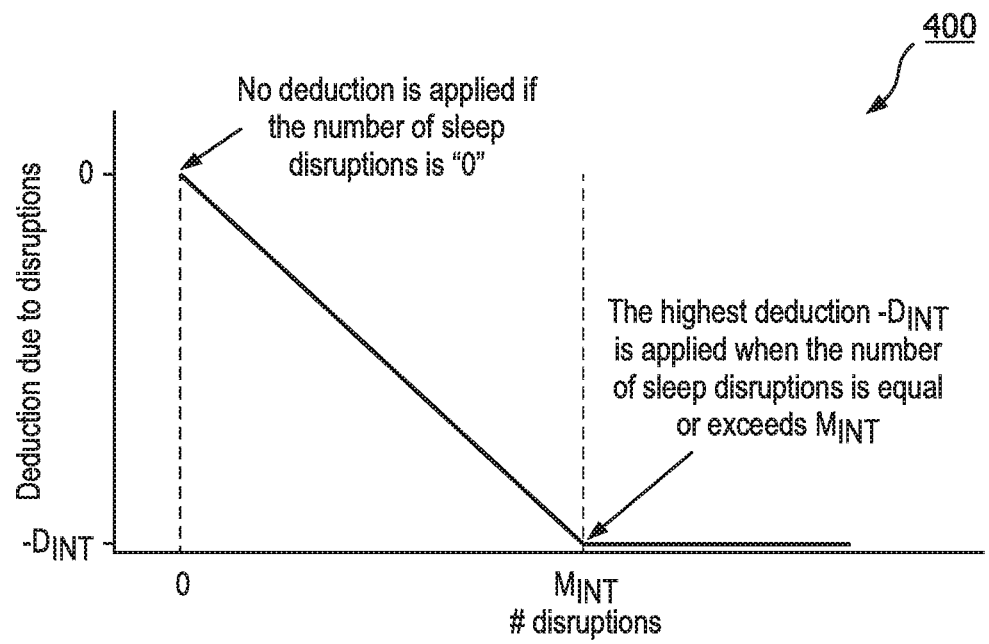
FIG. 4 is an illustrative graph of a deduction capable of being applied to determining a sleep session score value based on a number of sleep disruptions detected, in accordance with various embodiments.

FIG. 4 is an illustrative graph 400 of a deduction capable of being applied to determining a sleep session score value based on a number of sleep disruptions detected, in accordance with various embodiments. In a non-limiting embodiment, a sleep disruption is characterized as a period of wakefulness between a sleep on-set and a sleep off-set that is at least a certain amount of time in duration. For example, a period of wakefulness in excess of five minutes may correspond to a sleep disruption.

In one embodiment, deductions are applied based on a number of sleep disruptions that occur during a sleep session. A largest amount of deduction (e.g., $-D_{INT}$) is applied if the number of sleep disruptions is equal to or greater than a threshold number of disruptions 402 (e.g., $M_{INT}$). If no disruptions are detected during a sleep session, then a deduction of 0, or no deduction, is applied. For a number of disruptions greater than zero but less than threshold number 402, a deduction related to the number of disruptions is determined using Equation 4 and as seen by graph 400. In one example embodiment, a maximum deduction amount corresponds to a value of 6 for a number of disruptions equal to or greater than 3 (e.g., $-D_{INT}=6$, $-M_{INT}=3$), however persons of ordinary skill in the art will recognize that the aforementioned is merely exemplary.

$$Disruption_{Deduction} = \text{round}\left(\min\left\{0, \max\left\{-D_{INT}, -\frac{D_{INT} \times (\#\ of\ disruptions)}{-D_{INT}}\right\}\right\}\right).$$ Equation 4

Figure 5:
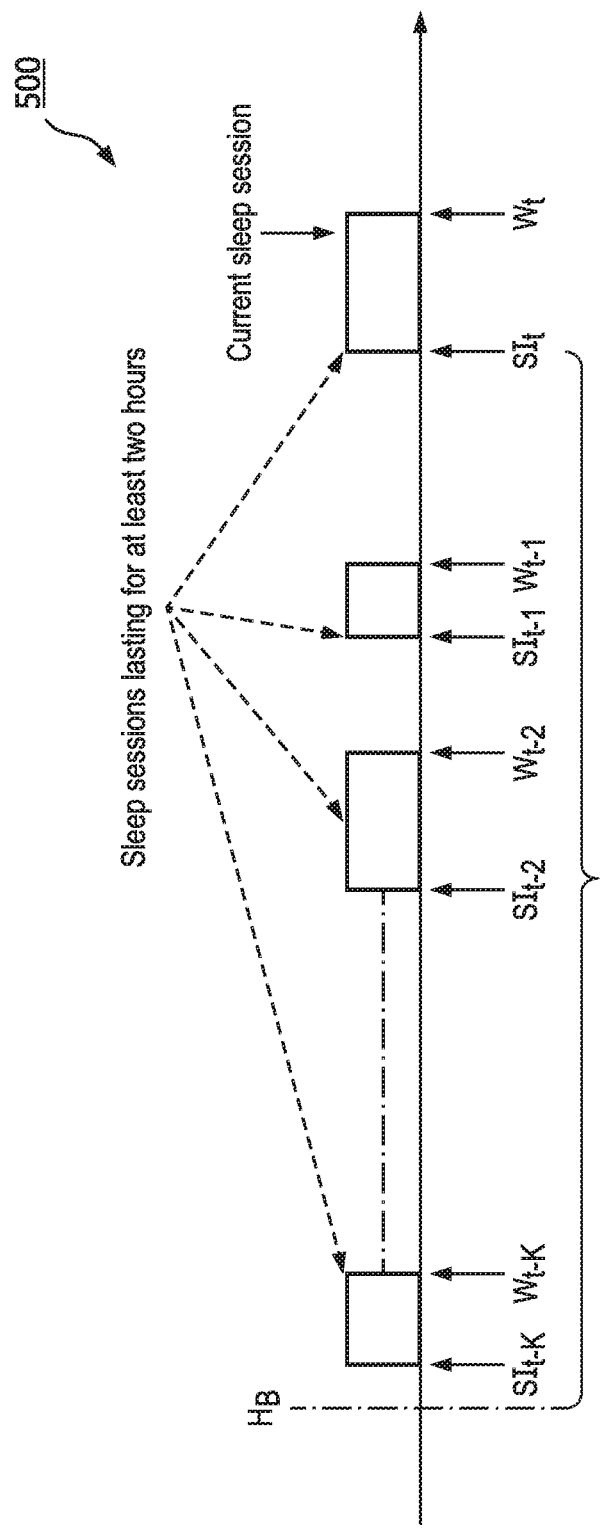
FIG. 5 is an illustrative graph of a deduction capable of being applied to determining a sleep session score value based on a sleep routine of an individual, in accordance with various embodiments.

FIG. 5 is an illustrative graph 500 of a deduction capable of being applied to determining a sleep session score value based on a sleep routine of an individual, in accordance with various embodiments. In one embodiment, a deduction based on user sleep regularity is applied. Regularity, for instance, is driven primarily by two factors: a time when a user goes to sleep (e.g., bedtime regularity), and a time when that user wakes up (wakeup time regularity).

Bedtime regularity is, in one embodiment, approximated by a regularity with regard to a detected sleep intention time. Sleep intention time, for instance, may be determined based on a difference between a detected sleep intention time and an average sleep intention time based all sleep sessions having a duration in excess of a first threshold in the last $d_H$-days. For example, any sleep session occurring in the last 7 days that is at least two hours long may be used to calculate a detected sleep intention time. In one embodiment, this sleep information is stored by user history database 140, and is accessible by sleep score assessment system 120 for determining the sleep intention time. In an embodiment, the sleep intention is input by user 170 using user device 110 and/or sleep score assessment system 120. For example, user 170 may input a sleep intention time for a particular sleep session into a mobile application running on sleep score assessment system 120.

Graph 500 illustrates one example use of user history to determine a sleep intention time. In the illustrative embodiment, $SI_{t-j}$ corresponds to a time stamp of a sleep intent for a j-th sleep session, $SI_t$ corresponds to a time stamp of a current sleep session, and $W_{t-j}$ corresponds to a time stamp of a wakeup time associated with the j-th sleep session. For example, user data obtained from sensor(s) 108 may include temporal metadata indicating times associated with that user activity. After determining when sleep begins using the user data, a corresponding time associated with that sleep onset may be obtained from the sleep metadata associated with the user data. In one example embodiment, $SI_{t-j}$ is measured in minutes, however persons of ordinary skill in the art will recognize that this is merely exemplary. Sleep wakeup time $W_{t-j}$, therefore, is determined using Equation 5:

$$W_{t-j}=SI_{t-j}+SOL_{t-j}+WASO_{t-j}+TST_{t-j}$$ Equation 5.

In Equation 5, SOL corresponds to a sleep onset latency, which is described in greater detail below. A history span, in one embodiment, to be used for determining an amount of user history sleep data to obtain from user history database 140 is described by Equation 6.

$$H_B = \begin{cases} \left[\text{floor}\left(\frac{SI_t}{1440}\right) - d_H - 0.5\right] \times 1440; & \mod(SI_t, 1440) < 720 \\ \left[\text{floor}\left(\frac{SI_t}{1440}\right) - d_H + 0.5\right] \times 1440; & \mod(SI_t, 1440) \geq 720 \end{cases}$$ Equation 6

As seen above, for a sleep session to be considered, $SI_{t-j} > H_B$. The deviation from average is determined using a time stamp difference $\Delta S_{t-j}$ with respect to a reference time (e.g., midnight), as seen below with reference to Equation 7, and using a deviation from the mean $BR_t$, as seen below with reference to Equation 8.

$$\Delta S_{t-j} = \begin{cases} \mod(SI_{t-j}, 1440); & \mod(SI_{t-j}, 1440) < 720 \\ \mod(SI_{t-j}, 1440) - 1440; & \mod(SI_{t-j}, 1440) \geq 720 \end{cases}$$ Equation 8

$$BR_t \begin{cases} 0; & K = 0 \\ \Delta S_t - \text{mean}([\Delta S_{t-1}, \ldots, \Delta S_{t-K}]); & K > 0 \end{cases}$$ Equation 9

Figure 6:
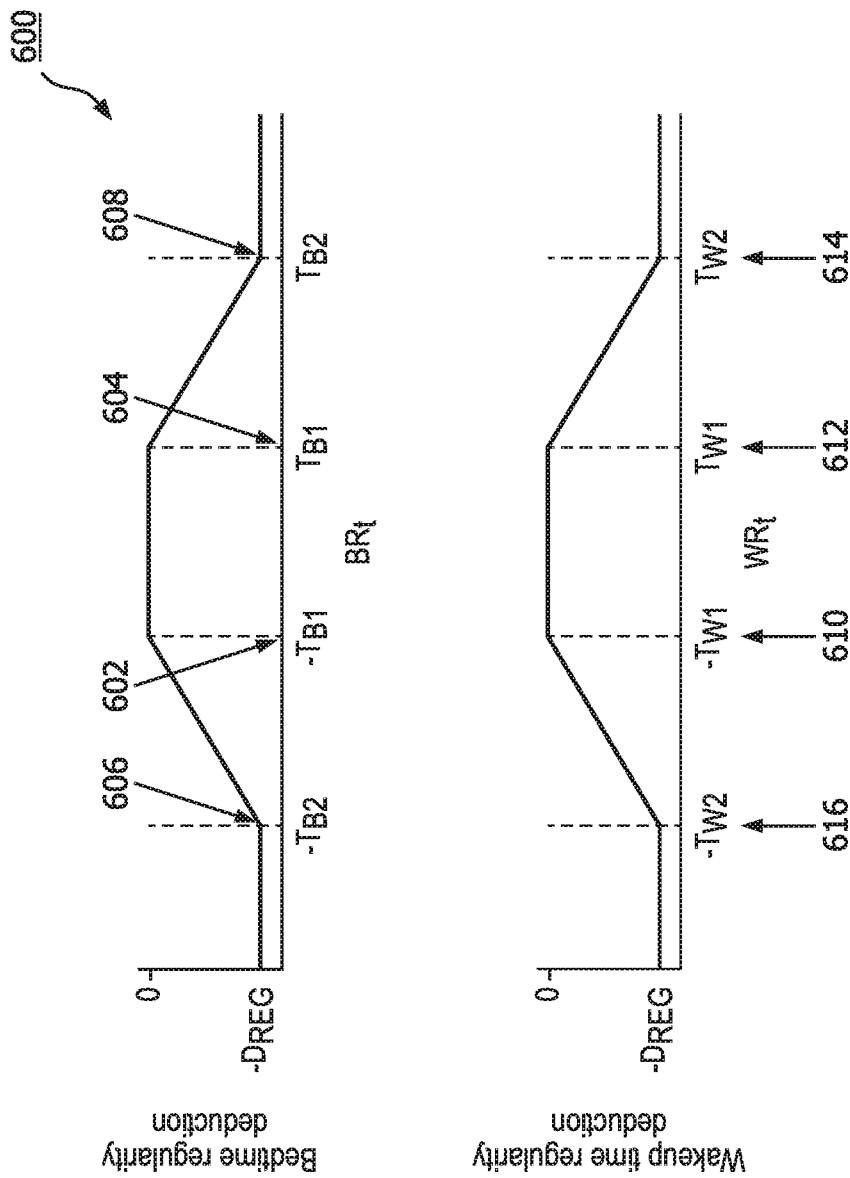
FIG. 6 is an illustrative graph illustrating how deductions are related to a difference in bedtime regularity, in accordance with various embodiments.

FIG. 6 is an illustrative graph 600 illustrating how deductions are related to a difference in bedtime regularity BRt, in accordance with various embodiments. In the non-limiting example embodiment, if a difference BRt is between a first threshold 602 (e.g., −TB1) and a second threshold 604 (e.g., +TB1), then no deduction or a zero deduction is applied. However, if a difference BRt is greater than or equal to a third threshold 606 or a fourth threshold 608 (e.g., ±TB2), then a maximum deduction DREG is applied. If BRt is between TB1 and TB2, then an amount of deduction to be applied is linearly related to BRt, for instance, as illustrated by Equation 10.

$$\text{Bedtime\_regularity\_deduction} = \text{round}\left(-\min\left\{D_{REG}, \max\left\{0, D_{REG} \times \frac{|BR_t| - T_{B1}}{T_{B2} - T_{B1}}\right\}\right\}\right).$$

Equation 10

Wakeup time regularity is determined, in one embodiment, using a similar technique as that of bedtime regularity. For example, a wakeup time difference is calculated using Equations 11 and 12:

$$\Delta W_{t-j} = \begin{cases} \mod(W_{t-j}, 1440); & \mod(W_{t-j}, 1440) < 720 \\ \mod(W_{t-j}, 1440) - 1440; & \mod(W_{t-j}, 1440) \geq 720 \end{cases}.$$

Equation 11

$$WR_t = \begin{cases} 0; & K = 0 \\ \Delta W_t - \text{mean}([\Delta W, \ldots, \Delta W_{t-K}]); & K > 0 \end{cases}.$$

Equation 12

If a difference $WR_t$ is between a first threshold 610 (e.g., −$T_{W1}$) and a Second threshold 612 (e.g., +$T_{W1}$), then no deductions are applied. A highest deduction $D_{REG}$ is applied if the difference is longer than a third threshold 616 (e.g., −$T_{W1}$), or a fourth threshold 618 (e.g., +$T_{W2}$). In one embodiment, the deduction is linearly scaled with $WR_t$, as described by Equation 13.

$$\text{Wakeup\_regularity\_deduction} = \text{round}\left(-\min\left\{D_{REG}, \max\left\{0, D_{REG} \times \frac{|WR_t| - T_{W1}}{T_{W2} - T_{W1}}\right\}\right\}\right).$$

Equation 13

In one example embodiment, a single regularity based deduction is applied. This allows a user to shift a bedtime and/or wakeup time together for any given sleep session, therefore only $D_{REG}$ is applied as a deduction, as described in Equation 14.

Sleep_routine_deduction=min(bedtime_deduction, wakeup_deduction+bedtime_deduction)    Equation 14.

Table 3 illustrates various example parameters that may be used for determining one or more of wakeup regularity deductions and bedtime regularity deductions.

TABLE 3

| Parameter | Default value |
| --- | --- |
| $d_H$ | 7 days |
| $D_{REG}$ | 5 |
| $T_{B1}$ | 20 minutes |
| $T_{B2}$ | 60 minutes |

TABLE 3-continued

| Parameter | Default value |
| --- | --- |
| $T_{W1}$ | 20 minutes |
| $T_{W2}$ | 60 minutes |

Figure 7:
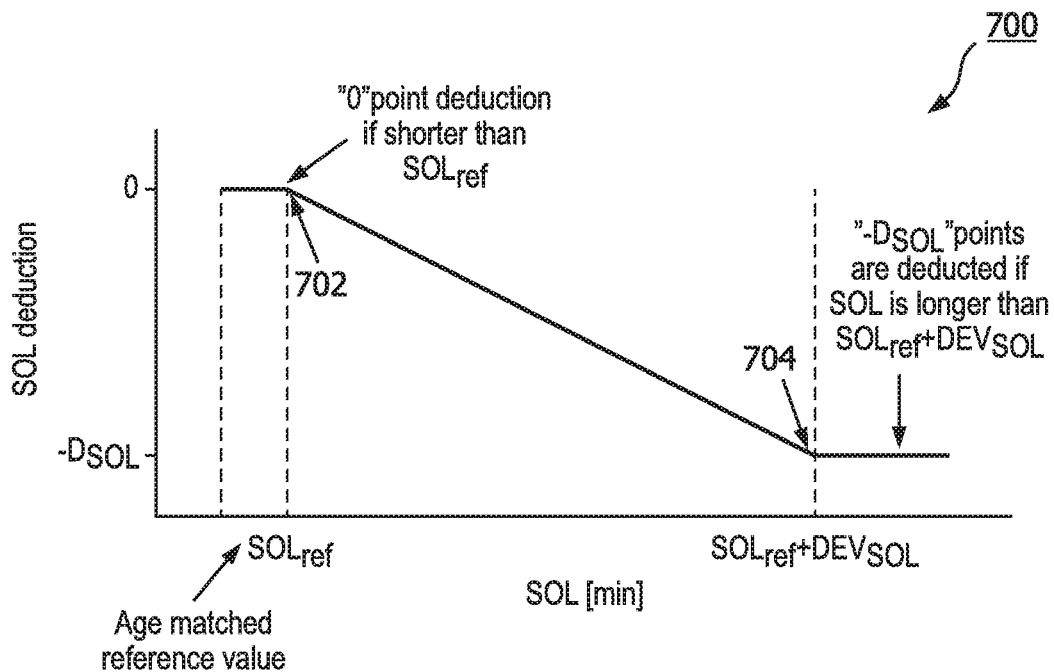
FIG. 7 is an illustrative graph of a deduction capable of being applied to determining a sleep session score value based on sleep onset latency, in accordance with various embodiments.

FIG. 7 is an illustrative graph 700 of a deduction capable of being applied to determining a sleep session score value based on sleep onset latency, in accordance with various embodiments. Sleep onset latency ("SOL"), as described herein, refers to an amount of time with which it takes for a user to fall asleep. A deduction associated with SOL, in one embodiment, depends on an age range associated with user 170. For instance, various age-based SOL deductions are stored by reference database 150, and these values are accessible by sleep score assessment system 120 to determine a sleep score for a user's sleep session.

In one embodiment, the age range indicates a maximum SOL deduction 702 (e.g., $SOL_{ref}$), capable of being applied when a sleep session score value is being determined. When the SOL that is detected exceeds a threshold 704 (e.g., $SOL_{ref}$ plus an amount $DEV_{SOL}$) the maximum deduction −$D_{SOL}$ is applied. If the SOL is less than second threshold 704, but greater than first threshold 702, then the deduction is, in one embodiment, linearly related to the SOL detected, as illustrated by Equation 15.

$$\text{SOL\_deduction} = \text{round}\left(\max\left\{-D_{SOL}, \min\left\{0, -\frac{D_{SOL} \times (SOL - SOL_{REF})}{DEV_{SOL}}\right\}\right\}\right).$$

Equation 15

Table 4 includes various exemplary values that are applicable for $SOL_{ref}$ depending on an age of a user. In one embodiment, reference database 150 stores values for $SOL_{ref}$ included within Table 4. Table 5 includes various exemplary values for $D_{SOL}$ and $DEV_{SOL}$, which, in one embodiment, are applied by sleep score assessment system 120 to determine a sleep score for a particular sleep session.

TABLE 4

| Age Range | $SOL_{ref}$ [minutes] |
| --- | --- |
| <30 | 15 |
| [30 to 40[ | 15 |
| [40 to 60[ | 17 |
| ≥60 | 20 |

TABLE 5

| Parameter | Default value |
| --- | --- |
| $D_{SOL}$ | 10 |
| $DEV_{SOL}$ | 30 minutes |

Figure 8:
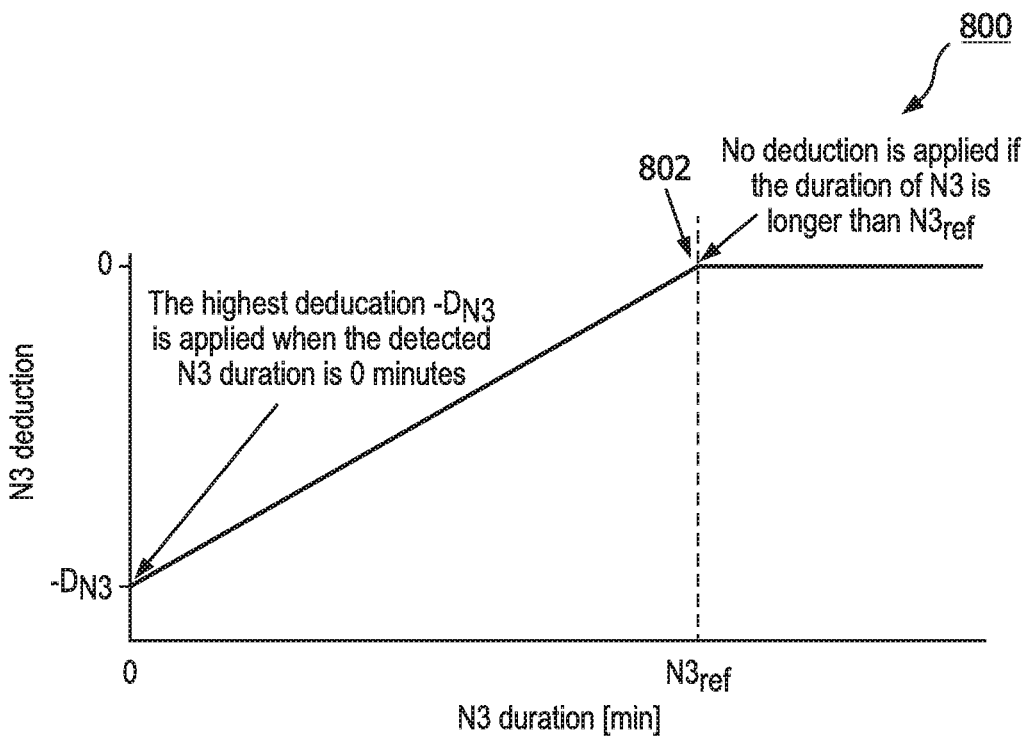
FIG. 8 is an illustrative graph of a deduction capable of being applied to determining a sleep session score value based on a duration of N3 sleep, in accordance with various embodiments.

FIG. 8 is an illustrative graph 800 of a deduction capable of being applied to determining a sleep session score value based on a duration of N3 sleep, in accordance with various embodiments. In the non-limiting embodiment, the deduction associated with N3 sleep duration, also referred to as a duration of deep sleep or slow-wave sleep, considers the recuperative value of sleep as being primarily driven by the presence of deep sleep. If, during a given sleep session, the duration of deep sleep does not meet an age matched reference threshold 802 (e.g., $N3_{ref}$), as seen below by Table 6, a deduction is applied. The deduction is linearly related, in one embodiment, to a duration of the N3 deep sleep for that particular sleep session. The maximum amount of deduction that can be applied, $D_{N3}$ corresponds to an N3 sleep duration of approximately 0 minutes. If, however, the detected duration of N3 sleep is greater than or equal to age matched reference threshold 802, no deductions are applied. The N3 based deductions are indicated below with reference to Equation 16. In Equation 10, N3 is the detected duration of N3 sleep and the default values for the parameters $N3_{ref}$ and $D_{N3}$ are listed in Table 6 and Table 7, respectively.

TABLE 6

| Age Range | $N3_{ref}$ [minutes] |
|---|---|
| >30 | 86 |
| [30 to 40[ | 72 |
| [40 to 60[ | 72 |
| ≥60 | 40 |

TABLE 7

| Parameter | Default value |
|---|---|
| $D_{N3}$ | 30 |

To prevent the deductions from lowering the score below a critical threshold M, a rescaling of the deductions needs to be applied when 100+Σdeduction<M. For instance, M may be defaulted to a value of 5 (e.g., M=5). The rescaling formulas ensure that the sleep session score value is at least equal to M, as well as ensuring that the sums of the deductions consistently add up, as described by Equation 11. In Equation 16, the deduction values after rescaling are referred to using the suffix "resc".

$$SOL\_ded\_resc = floor\left(\frac{M - 100}{TST_{ded} + WASO_{ded} + SOL_{ded} + Disruptions_{ded} + SleepRoutine_{ded} + N3_{ded}} \times SOL\_ded\right)$$

Equation 16

As an illustrative example of the rescaling procedure for the particular critical threshold value M=5, without rescaling the deductions associated with Table 8 would, in one embodiment, add up to −118. Therefore, if the initial sleep score value was set as being 100, the final sleep session score prior to any bonuses due to sleep interventions being applied, would be negative. The rescaling allows for the deductions to add up to −95 for critical threshold value M=5, such that the sleep session score value is no longer negative.

TABLE 8

| Type of deduction | Deduction before rescaling | Deduction after rescaling (using Eq. 11) |
|---|---|---|
| TST | −70 | −54 |
| WASO | −8 | −7 |
| SOL | −6 | −5 |
| Disruption | −12 | −10 |

TABLE 8-continued

| Type of deduction | Deduction before rescaling | Deduction after rescaling (using Eq. 11) |
|---|---|---|
| Sleep routine | −2 | −2 |
| N3 | −20 | −17 |

Figure 9:
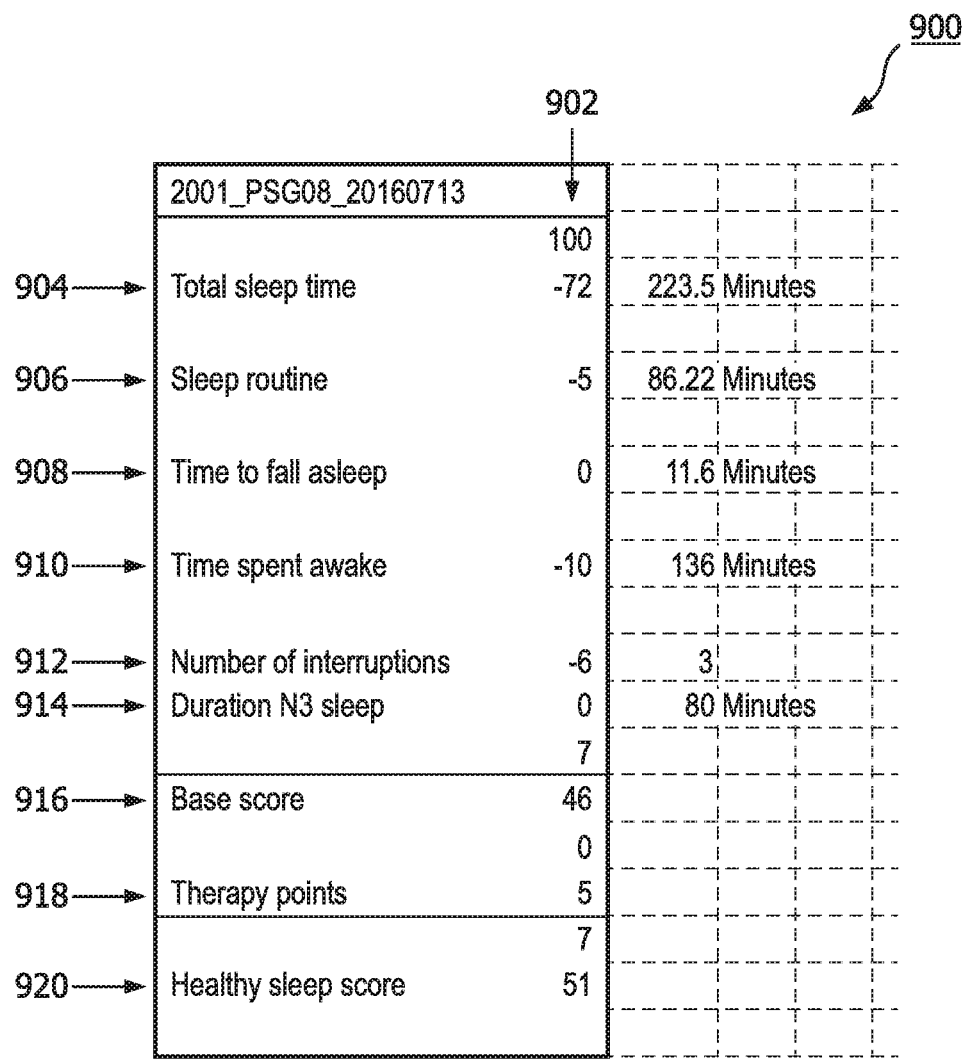
FIG. 9 is an illustrative diagram of an exemplary graphical user interface including a sleep session score and the various deductions capable of being applied, in accordance with various embodiments.

FIG. 9 is an illustrative diagram of an exemplary graphical user interface 900 including a sleep session score and the various deductions capable of being applied, in accordance with various embodiments. In the illustrative embodiment, graphical user interface 900, which is capable of being displayed by I/O interface 118 of sleep score assessment system 120, and/or any other suitable display device associated with sleep score assessment system 120, user device 110, and/or intervention device(s) 130, includes an initial sleep session score value 902, with which the deductions described above are capable of being applied to. For example, the initial sleep session score value may be set as 100.

In the illustrative embodiment, graphical user interface 900 further includes a total sleep time deduction 904, a sleep routine deduction 906, a time to fall asleep deduction 908, a time spent awake deduction 910, a number of sleep interruptions deduction 912, and a duration of N3 sleep deduction 914. As an example, each of deductions 904-914 are less than or equal to zero in value such that, when applied to initial sleep session score value 802, they reduce an amount of the sleep score.

A total base score 916 is determine by adding each deduction 904-914 to initial sleep session score value 902. In one embodiment, one or more bonus values, stemming from one or more sleep interventions, are also applied to the base/initial sleep session score value 902/818. The sleep interventions, as described in greater detail below, positively impact a sleep session's score. For example, if deductions 904-914 are negative in that they reduce a sleep session score value, the bonus(es) 918 is/are positive such that they increase the sleep session score value. A total sleep session score value 920, accounting for any deductions and/or bonus identified for a particular user's sleep session, is then determined. Persons of ordinary skill in the art will recognize that although graphical user interface 900 is displayed in a list type manner within FIG. 9, this is merely exemplary as alternative and/or additional display formats may be employed such as, but not limited to, graphs, tables, and/or any other suitable display mechanism, or any combination thereof.

Figure 10:
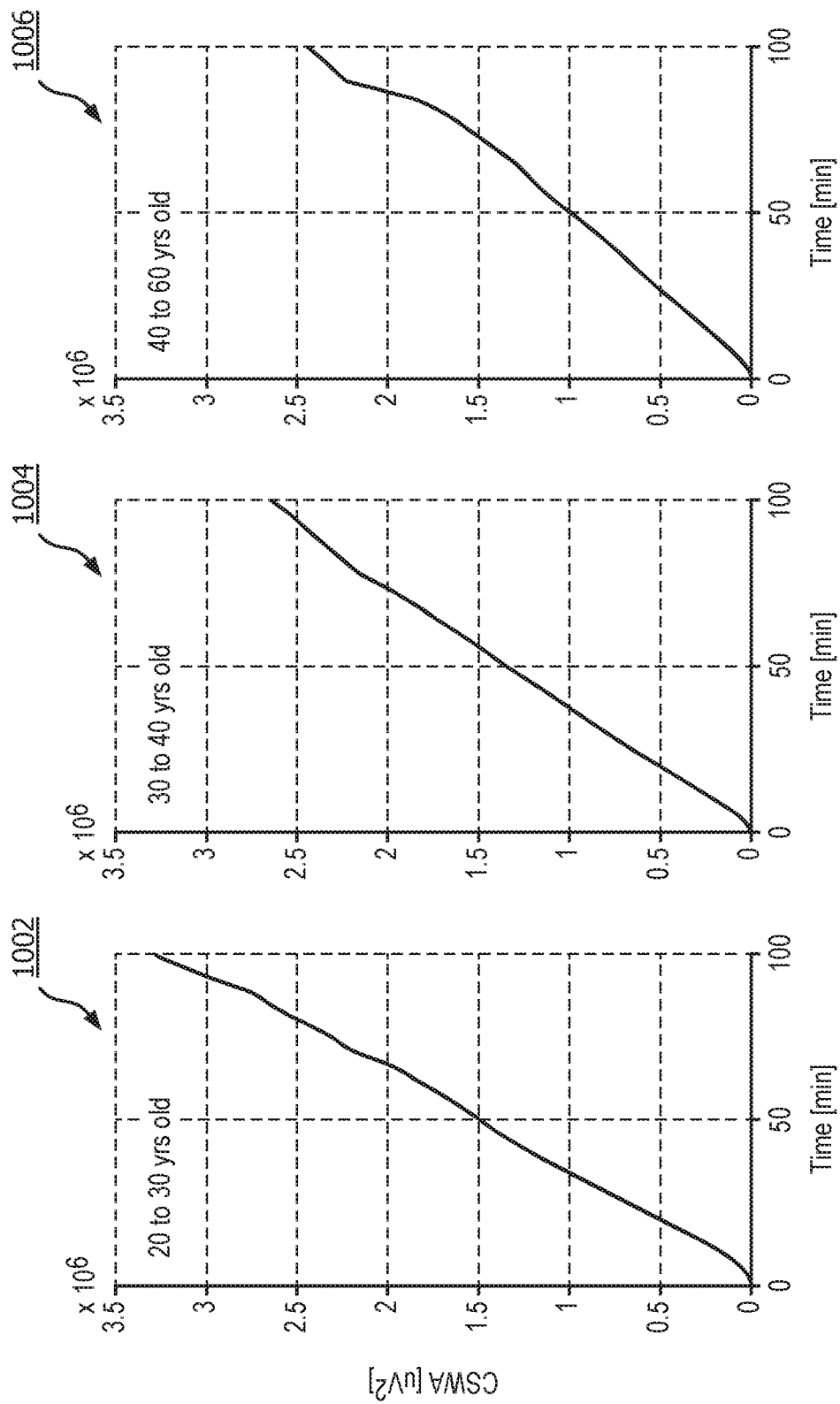
FIGS. 10A-C are illustrative graphs of a cumulative slow wave activity parameter for different age ranges, in accordance with various embodiments.

FIGS. 10A-C are illustrative graphs 1002-1006 of a cumulative slow wave activity ("CSWA") parameter for different age ranges, in accordance with various embodiments. In a non-limiting embodiment, interventions are capable of being provided to user 170 using intervention device(s) 130. For example, audible tones are capable of being provided using an auditory stimulation device. During EEG based detected non-rapid eye movement ("NREM") sleep, such audible tones are capable of being provided to enhance a restorative value of an individual's sleep by increasing an amplitude and amount of sleep slow waves, also referred to as delta waves, while not disturbing sleep. An amplitude and number of sleep slow waves correspond, in one embodiment, to slow wave activity ("SWA"), which corresponds to EEG power in the 0.5-4.0 Hz frequency band. A SWA accumulated over NREM sleep is useful, for example to quantify a restorative value of sleep that is provided.

In one embodiment, to determine an amount of bonus to be applied based on the intervention, a number of tones delivered, a ratio of detected NREM sleep/reference NREM sleep, and a ratio of the CSWA to a reference CSWA are all obtained. The ratio of detected NREM sleep to the reference NREM sleep, denoted by pNREM, is determined using age based values stored by reference database 150 and detailed below in Table 9.

TABLE 9

| Age Range | NREM reference [minutes] |
|---|---|
| <30 | 86 |
| [30 to 40[ | 72 |
| ≥40 | 72 |

In one embodiment, the ratio of CSWA to reference CSWA, denoted by $\rho_{SWA}$, is determined by dividing the CSWA associated with a current sleep session by the CSWA accumulated up during the duration of the detected NREM for an age group associated with user 170. As seen in FIGS. 10A-C, various example reference curves are shown for different age ranges. For instance, graph 1002 corresponds to CSWA values for an age range of 20 to 30 year old individuals, graph 1004 corresponds to CSWA values for an age range of 30 to 40 year old individuals, and graph 1006 corresponds to CSWA values for an age range of 40 to 60 year old individuals. The information associated with graphs 1002, 1004, and 1006 are capable of being stored by reference database 150 and accessed by sleep score assessment system 120 for determining a sleep score for user 170.

Figure 11:
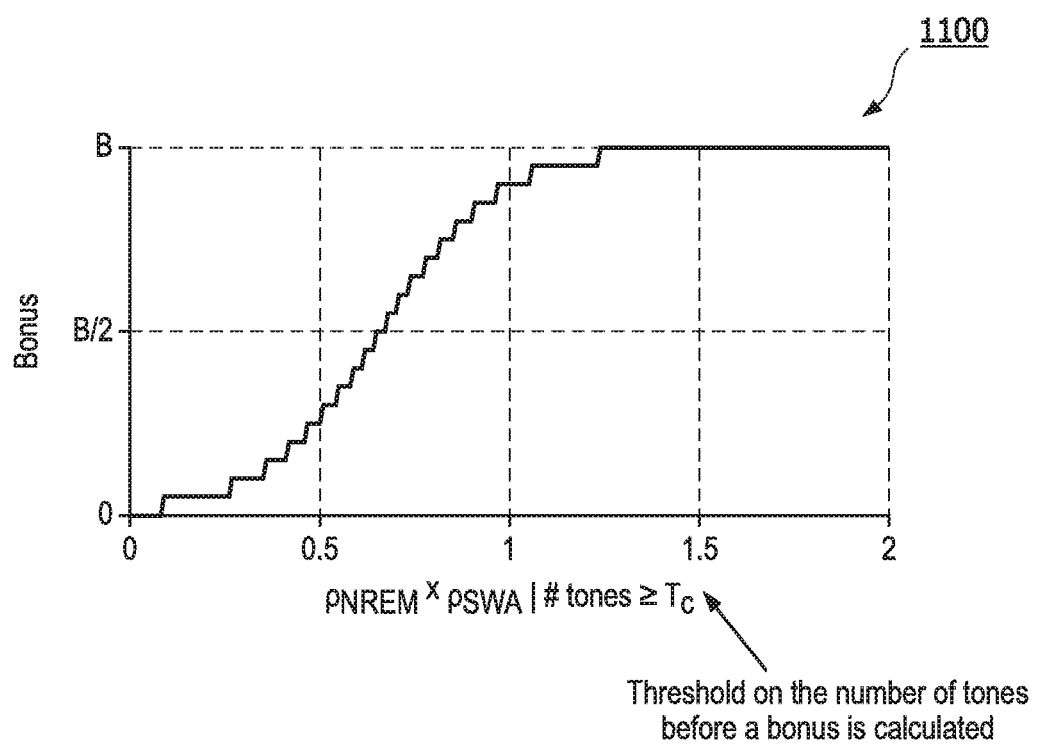
FIG. 11 is an illustrative graph of an amount of bonus capable of being applied for a sleep intervention, in accordance with various embodiments.

FIG. 11 is an illustrative graph 1100 of an amount of bonus capable of being applied for a sleep intervention, in accordance with various embodiments. In the illustrative embodiment, a product of the ratios $\rho_{NREM}$ and $\rho_{SWA}$ is determined, and used within Equation 17 to determine an amount of bonus to be applied to the sleep session score value.

$$\text{Bonus} = \begin{cases} 0; & \text{\# of tones} < T_c \\ \min\left(-\sum \text{Deductions, round}\left(\frac{B}{1 + \text{Exp}\left(\frac{B_a - 100 \times \rho_{NREM} \times \rho_{SWA}}{B_b}\right)}\right)\right); & T_c \leq \text{\# of tones}. \end{cases} \quad \text{Equation 17}$$

In Equation 17, $T_c$ corresponds to a critical number of tones that need to be provided by intervention device 130 (e.g., an auditory stimulation device) in order to have a bonus be applied to the sleep score for a user's sleep session. Furthermore, B corresponds to a maximum amount of bonus that is allowed to be applied to the sleep score. For instance, the value of B, in one embodiment, corresponds to a value less than or equal to a sum of the deductions such that the final sleep session score does not exceed the initial sleep session score.

In one embodiment, feedback provided by user 170 is also capable of being used to adjust an amount and magnitude of the deductions applied, as well as adjust an amount and magnitude of the bonuses applied. For example, user 170 may be provided with questions regarding aspects of their sleep session(s), which may be harnessed by sleep score assessment system 120 when determine subsequent sleep session scores. As another example, user 170 may be asked to provide daily activity tracking information to be used to determine biometric aspects associated with user 170 that may contribute to one or more aspects of his/her sleep. As an illustrative example, if sleep score assessment system 120 determines that user 170 is continually having sleep sessions scores that are less than a certain value, sleep score assessment system 120 may be prompted to ask one or more questions (e.g., via a graphical user interface displayed by a display screen), the answers of which may be used to adjust and/or calibrate the deduction parameters and/or the bonus parameters.

Figure 12:
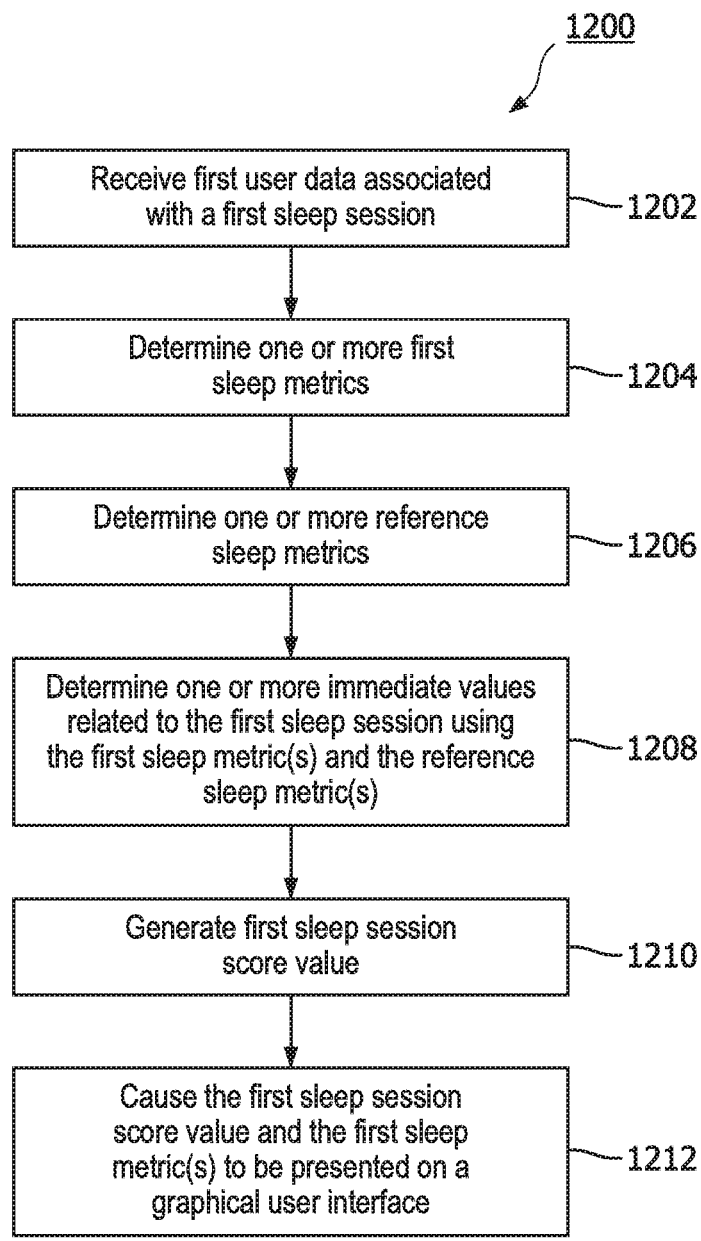
FIG. 12 is an illustrative flowchart of an exemplary process for generating a first sleep session score value, in accordance with various embodiments.

FIG. 12 is an illustrative flowchart 1200 of an exemplary process for generating a first sleep session score value, in accordance with various embodiments. In a non-limiting embodiment, process 1200 begins at operation 1202. At operation 1202, first user data associated with a first sleep session is received. For instance, first user data obtained by sensors 108 is obtained by user device 110, and the first user data is provided to sleep score assessment system 120 via network(s) 160. However, persons of ordinary skill in the art will recognize that user device 110 may include some or all of the functionality of sleep score assessment system 120, or sleep score assessment system 120 may include one or more sensors 108, and the use of one device to capture the user data and another device to process the data is merely exemplary. The first user data, in one embodiment, corresponds to data captured by sensor(s) 108 during a first sleep session of user 170. For example, sensor(s) 108 may monitor user activity during a period of time, which may include some periods of time associated with user 170 being asleep, and/or may include some periods time associated with user 170 being awake.

At operation 1204, one or more first sleep metrics is/are determined. The sleep metrics are associated with the first sleep session. In one embodiment, a sleep metric, as described herein, corresponds to a deduction that is capable of being applied to determine a sleep score. For example, the sleep metrics may correspond to deductions associated with a total sleep time, a total time spent away between a sleep onset time and a sleep offset time, a number of sleep disruptions that occurred during a sleep session, a sleep routine that depends on a regularity of sleep onset and wakeup times, a sleep onset latency, and/or a duration of N3 sleep. In one embodiment, the first sleep metrics are determined by sleep score assessment system 120 based on rules/instructions associated with sleep deductions 114 stored in memory 104, which are executed by processor(s) 102.

In one embodiment, data related to the sleep intervention(s) applied during a sleep session are stored such that sleep score assessment system 120 may analyze them. For instance, data related to a sensory stimulation delivered during a sleep session may be stored by sleep score assessment system 120. As one example, a number of tones provided by an auditory stimulation device (e.g., intervention device 130), may be tracked by the auditory stimulation device, and provided to sleep score assessment system 120. As another example, data related to audio/visual stimulation and/or electric/magnetic stimulation to facilitate sleep may also be tracked, as well as wake-up alarms.

At operation 1206, one or more reference sleep metrics is/are determined. The sleep metrics are, in one embodiment, based on prior user data obtained from one or more prior sleep sessions. For example, prior user data associated with prior sleep sessions may be stored by user history database 140. In response to receiving the first user data, sleep score assessment system 120 may request prior user data from user history database 140, which in turn may provide sleep score assessment system 120 with the prior user data. In one embodiment, the reference sleep metrics are alternatively stored by user history database 140, and therefore sleep score assessment system 120 is then provided with the reference sleep metric(s) in response to providing a request to user history database 140. In an example embodiment, the reference sleep metrics are associated with $d_H$ days prior to a current sleep session of user 170, as described in greater detail above with reference to FIG. 5.

At operation 1208, one or more immediate values related to the first sleep session is/are determined using the first sleep metric(s) and the reference sleep metric(s). In one embodiment, the immediate values are determined based on a comparison of the sleep metrics with the reference sleep metrics. For instance, a total time of sleep ("TST") deduction is determined based on a comparison between a current TST for the first sleep session and one or more thresholds 202, 204, and 206. As an illustrative example, if the TST for the first sleep session is less than second threshold 204 and greater than first threshold 202, then the TST deduction is linearly related to the TST for the first sleep session, as seen in greater detail with reference to FIG. 2. As another example, a wake after sleep onset ("WASO") deduction is determined based on a total WASO for the first sleep session. If the WASO for the first sleep session is greater than a first threshold 302, identified by an age associated with user 170, and stored by reference database 150, while also being less than a second threshold 304, then the WASO deduction is linearly related to the WASO, as described above with reference to FIG. 3.

At operation 1210, a first sleep session score value is generated. In one embodiment, the first sleep session score value is generated based on the immediate values related to the first sleep session. For instance, the deductions identified for the first sleep session are summed and applied to an initial sleep score value. As an illustrative example, an initial sleep score value is determined (e.g., the value 100), and each deduction determined during the first sleep session is applied to the initial sleep score value.

In one embodiment, the first sleep session score, the user data, the sleep metrics, and/or the reference sleep metrics are capable of being stored by user history database 140. For instance, user history database 140 is capable of updating the reference sleep metrics to include a recently obtained sleep metric, or metrics, such that the previous sleep history (e.g., $d_H$) includes the recent sleep session information. This allows for the reference sleep metrics to be updated to include the most recent values, and therefore be dynamically reconfigurable based on newly available data. Furthermore, this allows system 100 to learn how user 170 behaves over time, and update its models (e.g., instructions 114 and/or 116) based on recent metrics of user 170.

At operation 1212, the first sleep session score value and the first sleep metric(s) are presented on a graphical user interface. In one embodiment, the first sleep session score value and the first sleep metric(s) are displayed via a display device (e.g., I/O interface 118) of sleep score assessment system 120, however a graphical user interface including the first sleep session score value and the first sleep metric(s) alternatively are capable of being displayed on any suitable display device. As an illustrative example, graphical user interface 900 is displayed via a display screen (e.g., I/O interface 118), and includes a sleep session score value 918, as well as deductions 904-912, which are used to determine sleep session score value 918.

In one embodiment, additional user data representing at least one sleep metric associated with the first sleep session is also received. The additional user data is used to determine at least one sleep intervention that occurred during the first sleep session. For instance, one or more sleep interventions, such as one or more audible tones provided during the sleep session by an auditory stimulation device (e.g., intervention device 130 where intervention output component 112 corresponds to an auditory output device), one or more visual signals provided during the sleep session by a visual stimulation device (e.g., intervention device 130 where intervention output component 112 corresponds to a visual output component), and/or one or more environment interventions provided by an environment control device (e.g., intervention device 130 where intervention output component 112 corresponds to an environment output component), may have been provided. In response to determining that the sleep interventions occurred, sleep score assessment system 120 is configured to apply a second amount of measurements, such as a bonus, to the sleep score value. In some embodiments, the second amount of measurements is applied to an initial sleep score value, however persons of ordinary skill in the art will recognize that the measurements alternatively can be applied to the first sleep session score value.

Figure 13:
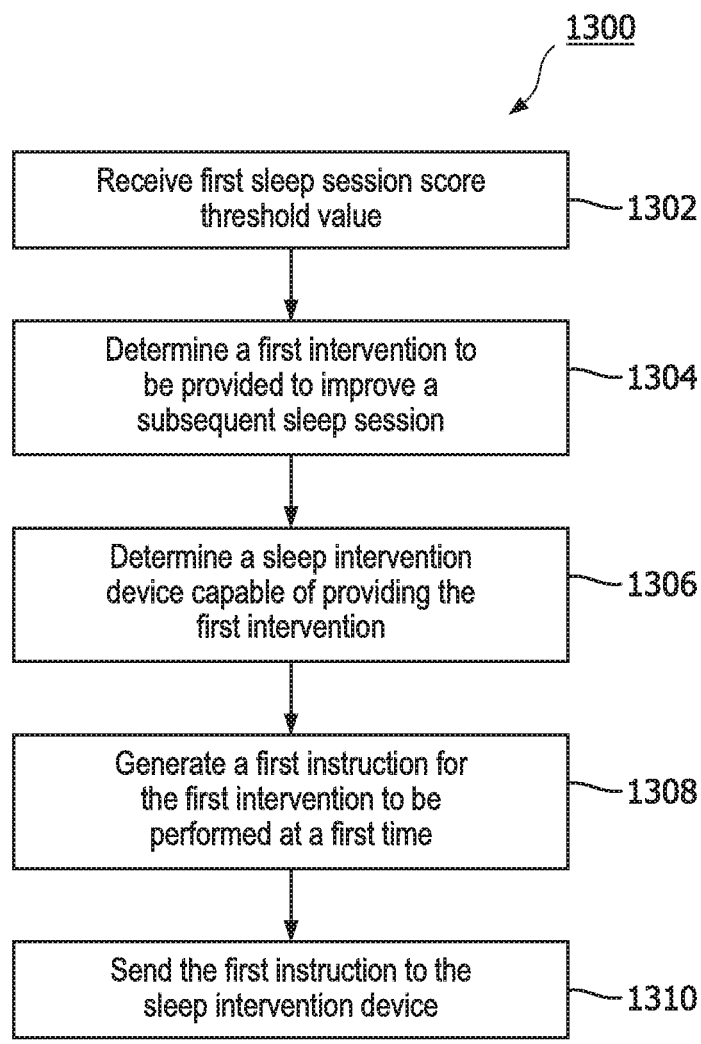
FIG. 13 is an illustrative flowchart of an exemplary process for determining a sleep intervention to be provided and sending an instruction for that sleep intervention to be provided at a particular time, in accordance with various embodiments.

FIG. 13 is an illustrative flowchart 1300 of an exemplary process for determining a sleep intervention to be provided and sending an instruction for that sleep intervention to be provided at a particular time, in accordance with various embodiments. In a non-limiting embodiment, process 1300 begins at operation 1302. At operation 1302, a first sleep session score threshold value is received. For instance, sleep session threshold values are capable of being stored by user history database 140 and/or reference database 150. The sleep session score threshold value is a parameter than indicates a quality of a sleep session score value. For example, if a sleep session score value exceeds the sleep session score threshold value, then that particular sleep session may be classified as being "good" sleep, whereas sleep session score values less than the sleep session score threshold value may be classified as being "poor" sleep. The particular value attributed to the threshold is capable of being set by user 170 and/or sleep score assessment system 120, and alternatively, the value is capable of being determined based on a history of sleep sessions score values of a user. For example, an average sleep session score value for a particular amount of time (e.g., one week, one month, etc.) may be used as the sleep session score threshold value, however persons of ordinary skill in the art will recognize that this is merely exemplary.

At operation 1304, a first intervention to be provided to improve a subsequent sleep session is determined. In one embodiment, the intervention that is determined is based, at least in part, on the first sleep session score value that was generated and/or the first sleep sessions score threshold value. For example, if the sleep session score value for a sleep session is determined to be less than the sleep session score threshold value, then sleep score assessment system 120 may determine that an intervention is needed. The particular type of intervention (e.g., audible tones, visual signals, environment controls, etc.) may be dependent on the sleep session score as well as, or alternatively, on the user's preference or other criteria. For example, a user may default to have audible tones be provided as a sleep intervention. As another example, a sleep session score value may indicate that a cooler temperature in the environment where the user sleeps would likely produce a higher sleep session score, and therefore may indicate that an environmental control intervention is to be selected.

At operation 1306, a sleep intervention device capable of providing the first intervention is determined. In one embodiment, the specific sleep intervention device 130 that is determined is based on, amongst other factors, the type of sleep intervention to be provided. For example, if audible tones are to be provided then an auditory stimulation device is to be determined as the intervention device 130 to provide the intervention. As another example, if a change of a temperature is to be provided, then an environmental control device may be determined as the intervention device 130.

At operation 1308, a first instruction for the first intervention to be performed at a first time is generated. The first instruction, for instance, is generated by sleep score assessment system 120. The particular time, or temporal window, with which the instruction is to be performed, may be based on the user data associated with the first sleep session. For example, if sleep score assessment system 120 determines that the intervention is to be provided at a particular time after sleep onset, then the instruction that is generated thereby may indicate that the time to perform the intervention should likely occur at a particular time, or during a particular temporal window, after a subsequent sleep session's sleep onset is detected. As another example, if the sleep intervention is to cause a temperature of a local environment where user 170 sleep to be lowered to a new temperature to stimulate sleep, then the instruction may be generated such that it causes the sleep intervention device (e.g., intervention device 130) to adjust the temperature in the local environment (e.g., by adjusting the temperature settings of a thermostat or other environmental control device) prior to a sleep onset time of user 170 based on a prior sleep session's sleep onset time and/or an average sleep onset time for user 170. At operation 1310, the first instruction is sent to the sleep intervention device such that the intervention is performed at prior to the prescribed time with which the intervention is to occur.

Figure 14:
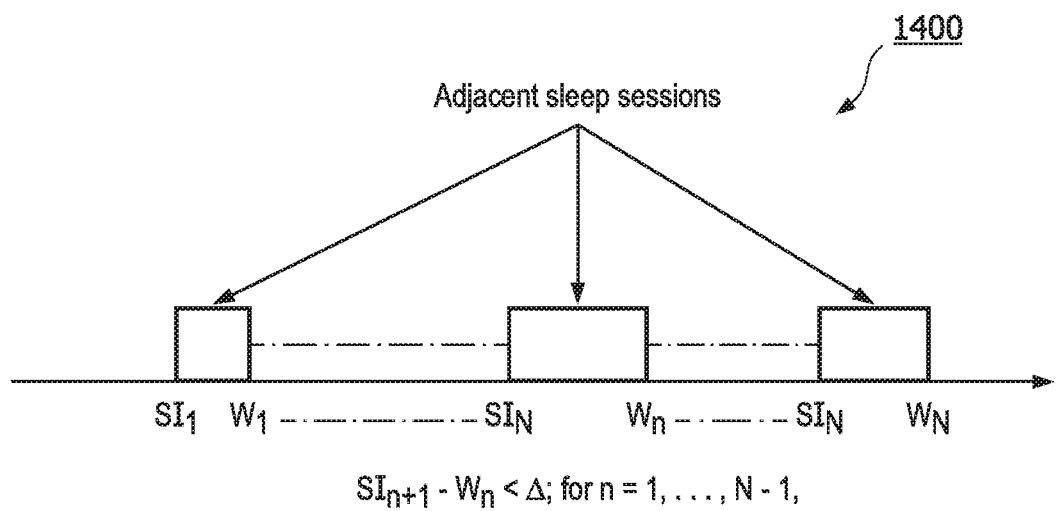

FIG. 14 is an illustrative graph 1400 of a deduction capable of being applied for determining a sleep session score value based on adjacent sleep sessions grouped together, in accordance with various embodiments. In one embodiment, adjacent sleep sessions are grouped together. For instance, two or more adjacent sleep sessions that are separated from each other by a time period shorter than $\Delta t$ minutes (e.g., $\Delta t = 120$ minutes) are grouped into a single sleep session. Graph 1400 includes N sleep sessions being consolidated together. The condition for grouping two or more adjacent sleep sessions, in one embodiment, that a timestamp of a sleep intent time of the "n+1" session $SI_{n+1}$ minus a timestamp of a wake time of the "n" session $W_n$ is smaller than $\Delta t$.

The sleep metrics resulting from the grouping of N adjacent sleep sessions are defined by Equations 18-24 in Table 10.

TABLE 10

| Consolidated parameter | Description | |
|---|---|---|
| Total sleep time | $\sum_{n=1}^{N} TST_n$ | Equation 18 |
| Wake after sleep onset | $\sum_{n=1}^{N} WASO_n + \sum_{n=1}^{N-1} \min(SO_{n+1} - W_n, \tau)$ where $SO_{n+1}$ is the sleep onset timestamp of the "n + 1" grouped session, and $\tau$ (<$\Delta$) is a configurable upper limit on the duration of the sleep session interruption (default value of $\tau$ is 60 minutes). | Equation 19. |
| Sleep onset latency | $\min(SOL_1, \ldots, SOL_N)$ | Equation 20. |
| Number of interruptions | $\sum_{n=1}^{N} INT_n$ where $INT_{n+k}$ is the number of interruptions of the (n + k) − th grouped sleep session. | Equation 21. |
| N3 sleep (deep sleep detected, dst) | $\sum_{n=1}^{N} N3_n$ | Equation 22. |
| CSWA (slow wave activity) | $\sum_{n=1}^{N} CSWA_n$ | Equation 23. |
| Number of tones | $\sum_{n=1}^{N} Tones_n$ | Equation 24. |

The additive approach applies for total sleep time, as described by Equation 18, the number of interruptions, as described by Equation 21, the detected N3 sleep, as described by Equation 22, the slow wave activity, as described by Equation 23, and the number of tones, as described by Equation 24. For sleep onset latency, the minimum across all grouped sleep sessions is used, as described by Equation 20. The wake after sleep onset duration is obtained by adding the WASO from grouped sleep sessions and adding the interval between wake and sleep onset of adjacent sleep sessions, as described by Equation 19. However, a threshold $\tau$ (<$\Delta t$) is used, in one embodiment, to limit the amount of WASO added for contiguous consolidated sleep sessions. Periods of wakefulness in between grouped sessions also may contribute to WASO, but these may not contribute to the number of interruptions in order to prevent double deductions being applied.

In one embodiment, the grouped sleep session contributes to the sleep routine deduction using the sleep intent of the first grouped session $SI_1$ and the wake of the last grouped session $W_N$ as sleep intent and wake timestamps. For instance, for a grouped session the equation: Wakeup time=Sleep intent+Sleep onset latency+Wake after sleep onset+total sleep time may not provide accurate results based on the cap on WASO described in Equation 19. After grouping the adjacent sleep session, a date is assigned and used as sleep intent of the grouped session $SI_1$.

The grouping of adjacent sleep sessions, in one embodiment, considers sleep sessions of a same nature (i.e. either baseline or therapy). This means that a baseline sleep session and a therapy sleep session should not be grouped together even if they are separated by an amount of time less than the threshold Δt. In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method for facilitating sleep improvement for a user, comprising:
   receiving, from one or more sensors, first user data associated with a first sleep session of a user;
   determining, based on the first user data, one or more first sleep metrics associated with the first sleep session;
   obtaining prior user data of the user from one or more prior sleep sessions;
   determining one or more reference sleep metrics, the one or more reference sleep metrics being based on the obtained prior user data;
   determining one or more sleep score deductions including first sleep score deductions associated with the first sleep session based on the determined one or more first sleep metrics and the one or more reference sleep metrics;
   wherein the one or more first sleep metrics include at least information indicating a sleep routine of the user, wherein the sleep routine of the user depends on a regularity of sleep onset time and/or a regularity of wakeup time, wherein the one or more sleep score deductions are also determined based on at least the regularity of sleep onset time and/or the regularity of wakeup time;
   determining an updated first sleep session score value based on an initial first sleep session score value and the first sleep score deductions associated with the first sleep session, wherein the updated first sleep session score value is less than or equal to the initial first sleep session score value;
   determining, based on the updated first sleep session score value, a first sleep intervention to be provided to the user; and
   causing a sleep intervention device to provide the first sleep intervention during a subsequent sleep session, wherein the sleep intervention device includes a memory comprising instruction data representing a set of instructions, at least one sleep intervention output component that is configured to adjust a parameter of a local environment with which the user is located, and a processor configured to communicate with the memory and the at least one sleep intervention output component and to execute the set of instructions, wherein the set of instructions, when executed by the processor, cause the sleep intervention device, including the at least one sleep intervention output component, to provide the first sleep intervention, which is determined based on the updated first sleep session score value, during the subsequent sleep session.

2. The method of claim 1, further comprising:
   receiving, from the one or more sensors, second user data associated with the first sleep session;
   determining, based on the second user data, one or more second sleep metrics associated with the first sleep session;
   determining, based on the one or more second sleep metrics, one or more previous sleep interventions that occurred during the first sleep session; and
   determining one or more second sleep score deductions related to the first sleep session based on the one or more previous sleep interventions,
   wherein the updated first sleep session score value is further based on the one or more second sleep score deductions.

3. The method of claim 2, wherein the at least one sleep intervention output component includes an auditory stimulation device, a visual stimulation device and/or an environmental control device,
   wherein the one or more previous sleep interventions comprise at least one of:
   at least one audible tone provided during the first sleep session by the auditory stimulation device;
   at least one visual signal provided during the first sleep session by the visual stimulation device; and
   at least one environmental intervention provided by the environmental control device.

4. The method of claim 1, further comprising:
   receiving a first sleep session score threshold value,
   wherein the first sleep intervention is further determined based on the first sleep session score threshold value;
   generating a first instruction for the first sleep intervention to be performed at a first time based on the first user data; and
   sending the first instruction to the at least one sleep intervention device prior to the first time.

5. The method of claim 1, wherein the one or more first sleep metrics comprise at least one of:
   first information associated with at least one first temporal duration of at least one sleep stage that occurred during the first sleep session;
   second information associated with a first amount of time that the user experienced a wake period during the first sleep session;
   a first number of sleep disruption events;
   third information indicating a second amount of time associated with a latency of sleep onset for the first sleep session; and
   fourth information indicating an approximate wake-up time associated with the first sleep session.

6. The method of claim 1, wherein determining the one or more reference sleep metrics further comprises at least one of:
   receiving, from a user sleep history database, the prior user data obtained from the one or more prior sleep sessions; and receiving, from a reference sleep database, reference user data representing one or more sleep parameters associated with the user.

7. The method of claim 1, further comprising: storing, using a user history database, at least one of: the first user data, the one or more first sleep metrics, and the first sleep session score value,
wherein the one or more reference sleep metrics are updated based, at least in part, on the at least one of: the first user data, the one or more first sleep metrics, and the first sleep session score value.

8. The method of claim 1, further comprising:
receiving feedback data representing feedback to at least one user inquiry provided to the user;
determining, based on the feedback data, one or more second sleep score deductions,
wherein the updated first sleep session score value is further based on the one or more second sleep score deductions; and
storing the one or more second sleep score deductions to be applied to generation of one or more subsequent sleep session score values.

9. The method of claim 8, wherein the first sleep intervention is further determined based on the one or more second sleep score deductions.

10. The method of claim 1, wherein the first sleep score deductions include a first sleep score deduction value corresponding to a first sleep metric associated with the first sleep session, and
wherein determining the first sleep score deduction value is based on a comparison of the first sleep metric with a first reference sleep metric.

11. The method of claim 1, wherein the one or more sleep score deductions include positive sleep score deductions, and
wherein each of the one or more sleep score deductions is subtracted from the initial sleep session score value to obtain the updated sleep session score value.

12. The method of claim 1, wherein the one or more sleep score deductions include negative sleep score deductions, and
wherein each of the one or more sleep score deductions is added to the initial sleep session score value to obtain the updated sleep session score value.

13. The method of claim 1,
wherein the first sleep score deductions are related to a difference in the regularity of sleep onset time and/or a difference in the regularity of wakeup time.

14. The method of claim 13, wherein, if the difference in the regularity of sleep onset time and/or the difference in the regularity of wakeup time is between an associated first threshold value and an associated second threshold value, then no first sleep score deduction or a zero first sleep score deduction is applied.

15. The method of claim 14, wherein, if the difference in the regularity of sleep onset time and/or the difference in the regularity of wakeup time is greater than or equal to an associated third threshold value or an associated fourth threshold value, then a maximum first sleep score deduction is applied.

16. The method of claim 15, wherein, if the difference in the regularity of sleep onset time is between the associated first threshold value and the associated third threshold value or if the difference in the regularity of sleep onset time is between the associated second threshold value and the associated fourth threshold value, then an amount of first sleep score deduction to be applied is linearly related to the difference in the regularity of sleep onset time using the below Equation:

$$\text{Bedtime}_{regularity_{deduction}} = \text{round}\left(-\min\left\{D_{REG}, \max\left\{0, D_{REG} \times \frac{BR_t - T_{B1}}{T_{B2} - T_{B1}}\right\}\right\}\right)$$

where $D_{REG}$ is the maximum first sleep score deduction for the regularity of sleep onset time,
$BR_t$ is the difference in the regularity of sleep onset time,
$T_{B1}$ is the first threshold value for the regularity of sleep onset time, and
$T_{B2}$ is the second threshold value for the regularity of sleep onset time.

17. The method of claim 15, wherein, if the difference in the regularity of wakeup time is between the associated first threshold value and the associated third threshold value or if the difference in the regularity of sleep onset time is between the associated second threshold value and the associated fourth threshold value, then an amount of first sleep score deduction to be applied is linearly related to the difference in the regularity of wakeup time using the below Equation:

$$\text{Wakeup\_regularity\_deduction} = \text{round}\left(-\min\left\{D_{REG}, \max\left\{0, D_{REG} \times \frac{|WR_t| - T_{W1}}{T_{W2} - T_{W1}}\right\}\right\}\right)$$

where $D_{REG}$ is the maximum first sleep score deduction for the regularity of wakeup time,
$WR_t$ is the difference in the regularity of wakeup time,
$T_{B1}$ is the first threshold value for the regularity of wakeup time, and
$T_{B2}$ is the second threshold value for the regularity of wakeup time.

18. A system for facilitating sleep improvement for a user, the system comprising:
memory;
communications circuitry; and
one or more processors configured by machine-readable instructions stored by the memory to:
receive, from one or more sensors, first user data associated with a first sleep session of a user;
determine, based on the first user data, one or more first sleep metrics associated with the first sleep session;
obtain prior user data of the user from one or more prior sleep sessions;
determine one or more reference sleep metrics, the one or more reference sleep metrics being based on the prior user data obtained from one or more prior sleep sessions;
determine one or more sleep score deductions including first sleep score deductions associated with the first sleep session based on the determined one or more first sleep metrics and the one or more reference sleep metrics;
wherein the one or more first sleep metrics include at least information indicating a sleep routine of the user, wherein the sleep routine of the user depends on a regularity of sleep onset time and/or a regularity of wakeup time, wherein the one or more sleep score deductions are also determined based on at least the regularity of sleep onset time and/or the regularity of wakeup time;

determine an updated first sleep session score value based on an initial first sleep session score value and the first sleep score deductions associated with the first sleep session, wherein the updated first sleep session score value is less than or equal to the initial first sleep session score value;

determine, based on the updated first sleep session score value, a first sleep intervention to be provided to the user; and cause a sleep intervention device to provide the first sleep intervention during a subsequent sleep session, wherein the sleep intervention device includes a memory comprising instruction data representing a set of instructions, at least one sleep intervention output component that is configured to adjust a parameter of a local environment with which the user is located, and a processor configured to communicate with the memory and the at least one steep intervention output component and to execute the set of instructions, wherein the set of instructions, when executed by the processor, cause the sleep intervention device, including at least one sleep intervention output component, to provide the first sleep intervention, which is determined based on the updated first sleep session score value, during the subsequent sleep session.

19. The system of claim 18, wherein the one or more processors is further configured by the machine-readable instructions to:

receive, from the one or more sensors, second user data associated with the first sleep session;

determine, based on the second user data, one or more second sleep metrics associated with the first sleep session;

determine, based on the one or more second sleep metrics, one or more previous sleep interventions that occurred during the first sleep session; and determine one or more second sleep score deductions related to the first sleep session based on the one or more previous sleep interventions, wherein the updated first sleep session score value is further based on the one or more second sleep score deductions.

20. The system of claim 19, wherein the at least one sleep intervention output component includes an auditory stimulation device, a visual stimulation device and/or an environmental control device, wherein the one or more previous sleep interventions comprise at least one of:

at least one audible tone provided during the first sleep session by the auditory stimulation device;

at least one visual signal provided during the first sleep session by the visual stimulation device; and at least one environmental intervention provided by the environmental control device.

21. The system of claim 18, wherein the one or more processors is further configured by the machine-readable instructions to:

receive a first sleep session score threshold value, wherein the first sleep intervention is further determined based on the first sleep session score threshold value;

generate a first instruction for the first sleep intervention to be performed at a first time based on the first user data; and send the first instruction to the sleep intervention device prior to the first time.

22. The system of claim 18, wherein the one or more first sleep metrics comprise at least one of:

first information associated with at least one first temporal duration of at least one sleep stage that occurred during the first sleep session;

second information associated with a first amount of time that the user experienced a wake period during the first sleep session;

a first number of sleep disruption events;

third information indicating a second amount of time associated with a latency of sleep onset for the first sleep session; and fourth information indicating an approximate wake-up time associated with the first sleep session.

23. The system of claim 18, the one or more processors being configured to determine the one or more reference sleep metrics further comprises the one or more processors to be configured by the machine-readable instructions to at least one of:

receive, from a user sleep history database, the prior user data obtained from the one or more prior sleep sessions; and receive, from a reference sleep database, reference user data representing one or more sleep parameters associated with the user.

24. The system of claim 18, wherein the one or more processors is further configured by the machine-readable instructions to: store, using a user history database, at least one of: the first user data, the one or more first sleep metrics, and the first sleep session score value, wherein the one or more reference sleep metrics are updated based, at least in part, on the at least one of: the first user data, the one or more first sleep metrics, and the first sleep session score value.

25. The system of claim 18, wherein the one or more processors is further configured by the machine-readable instructions to:

receive feedback data representing feedback to at least one user inquiry provided to the user;

determine, based on the feedback data, one or more second sleep score deductions, wherein the updated first sleep session score value is further based on the one or more second sleep score deductions; and store the one or more second sleep score deductions to be applied to generation of one or more subsequent sleep session score values.

26. The system of claim 25, wherein the first sleep intervention is further determined based on the one or more second sleep score deductions.

27. The system of claim 18, wherein the first sleep score deductions include a first sleep score deduction value corresponding to a first sleep metric associated with the first sleep session, and wherein determining the first sleep score deduction value is based on a comparison of the first sleep metric with a first reference sleep metric.

28. The system of claim 18, wherein the one or more sleep score deductions include positive sleep score deductions, and wherein each of the one or more sleep score deductions is subtracted from the initial sleep session score value to obtain the updated sleep session score value.

29. The system of claim 18, wherein the one or more sleep score deductions include negative sleep score deductions, and
wherein each of the one or more sleep score deductions is added to the initial sleep session score value to obtain the updated sleep session score value.

30. A system configured to facilitate sleep improvement for a user, the system comprising:
means for receiving, from one or more sensors, first user data associated with a first sleep session of a user;
means for determining, based on the first user data, one or more first sleep metrics associated with the first sleep session;
means for obtaining prior user data of the user from one or more prior sleep sessions;
means for determining one or more reference sleep metrics, the one or more reference sleep metrics being based on the prior user data obtained from one or more prior sleep sessions;
means for determining one or more sleep score deductions including first sleep score deductions associated with the first sleep session based on the determined one or more first sleep metrics and the one or more reference sleep metrics;
wherein the one or more first sleep metrics include at least information indicating a sleep routine of the user, wherein the sleep routine of the user depends on a regularity of sleep onset time and/or a regularity of wakeup time, wherein the one or more sleep score deductions are also determined based on at least the regularity of sleep onset time and/or the regularity of wakeup time,
means for determining an updated first sleep session score value based on an initial first sleep session score value and the first sleep score deductions associated with the first sleep session, wherein the updated first sleep session score value is less than or equal to the initial first sleep session score value;
means for determining, based on the updated first sleep session score value, a first sleep intervention to be provided to the user; and
means for causing a sleep intervention device to provide the first sleep intervention during a subsequent sleep session, wherein the sleep intervention device includes a memory comprising instruction data representing a set of instructions, at least one sleep intervention output component that is configured to adjust a parameter of a local environment with which the user is located, and a processor configured to communicate with the memory and the at least one sleep intervention output component and to execute the set of instructions, wherein the set of instructions, when executed by the processor, cause the sleep intervention device, including the at least one sleep intervention output component, to provide the first sleep intervention, which is determined based on the updated first sleep session score value, during the subsequent sleep session.

31. The sleep score assessment system of claim 30, further comprising:
means for receiving a first sleep session score threshold value, wherein the first sleep intervention is further determined based on the first sleep session score threshold value;
means for generating a first instruction for the first sleep intervention to be performed at a first time based on the first user data; and
means for sending the first instruction to the sleep intervention device prior to the first time.

32. The system of claim 30, wherein the first sleep score deductions include a first sleep score deduction value corresponding to a first sleep metric associated with the first sleep session, and
wherein determining the first sleep score deduction value is based on a comparison of the first sleep metric with a first reference sleep metric.

33. The system of claim 30, wherein the one or more sleep score deductions include positive sleep score deductions, and
wherein each of the one or more sleep score deductions is subtracted from the initial sleep session score value to obtain the updated sleep session score value.

34. The system of claim 30, wherein the one or more sleep score deductions include negative sleep score deductions, and
wherein each of the one or more sleep score deductions is added to the initial sleep session score value to obtain the updated sleep session score value.

* * * * *